(12) United States Patent
Zhang et al.

(10) Patent No.: US 7,252,989 B1
(45) Date of Patent: Aug. 7, 2007

(54) ADENOVIRUS SUPERVECTOR SYSTEM

(75) Inventors: Wei-Wei Zhang, Sugar Land, TX (US); Jack Roth, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 08/222,285

(22) Filed: Apr. 4, 1994

(51) Int. Cl.
*C12N 15/00* (2006.01)
*C07H 21/02* (2006.01)

(52) U.S. Cl. .................................. 435/320.1; 536/23.1
(58) Field of Classification Search .................. 514/44; 435/320.1, 240.1, 69.1
See application file for complete search history.

(56) References Cited

U.S. PATENT DOCUMENTS 4,683,202 A    7/1987   Mullis

FOREIGN PATENT DOCUMENTS

| FR | 2688514 | 9/1993 |
|---|---|---|
| WO | WO 93/03769 | 3/1993 |
| WO | WO 94/10323 | 5/1994 |
| WO | WO 94/24297 | 10/1994 |
| WO | WO 95/02697 | 1/1995 |
| WO | WO 95/29993 | 11/1995 |

OTHER PUBLICATIONS

Newalt et al., Behavioral and Brain Sciences, 18 : 1-9 (1995).*
Wolff, Current Biology, 3 : 743-748 (1993).*
Yang et al., Proc. Natl. Acad. Sci. USA, 91(10):4407-4411 (1994).*
Graham et al, Methods in Molecular Biology, 7:109-128 (1991).*
Davidson et al, Nature Genetics, 3:219-223 (1993).*
Engelhardt et al, Proc. Natl. Acad. Sci. USA, 91:6196-6200 (1994).*
Klessig et al, Molecular and Cellular Biology, 4(7):1354-1362 (1984).*
Wang et al. (1996) Nature Med. 2, 714-716.*
Brough et al. (1992) Viral. 190, 624-634.*
Berkner, K.L. Development of adenovirus vectors for the expression of heterologous genes. *BioTechniques* 6:616-629, 1988.
Blau, "Muscling in on gene therapy", *Nature*, 364:673-675, 1993.
Bridge, E., S. Medghalchi, S. Ubol, M. Leesong, and G. Ketner. Adenovirus early region 4 and viral DNA synthesis. *Virology* 193:794-801, 1993.
Friedmann, T. Gene therapy of cancer through restoration of tumor-suppressor functions? *CANCER* 70(Suppl) :1810-1817, 1992.
Glorioso, J.G., W.F. Goins, and D.J. Fink. Herpes simplex virus-based vectors. *Semin. Virol.* 3:265-276, 1992.
Gomez-Foix, A.M., W.S. Coats, S. Baque, T. Alam, R.D. Gerard, and C.B. Newgard. Adenovirus-mediated transfer of the muscle glycogen phosphorylase gene into hepatocytes confers altered regulation of glycogen. *J. Biol. Chem.* 267:25129-25134, 1992.
Graham, F.L., and L. Prevec. Adenovirus-based expression vectors and recombinant vaccines. *Biotechnology* 20:363-390, 1992.
Grunhaus, A., and M.S. Horwitz. Adenoviruses as cloning vectors. *Semin. Virol.* 3:237-252, 1992.

Hearing, P., R.J. Samulski, W.L. Wishart, and T. Shenk. Identification of a repeated sequence element required for efficient encapsidation of the adenovirus type 5 chromosome. *J. Virol.* 61:2555-2558, 1987.
Hermonat, P.L., and N. Muzyczka. Use of adeno-associated virus as a mammalian DNA cloning vector: transduction of neomycin resistance into mammalian tissue culture cells. *Proc. Natl. Acad. Sci. USA* 81:6466-6470, 1984.
Herz, J., and R.D. Gerard. Adenovirus-mediated transfer of low density lipoprotein receptor gene acutely accelerates cholesterol clearance in normal mice. *Proc. Natl. Acad. Sci. USA* 90:2812-2816, 1993.
Jaffe et al., "Adenovirus-mediated in vivo gene transfer and expression in normal rat liver", *Nature Genetics*, 1:372-378, 1992.
Ketner et al., "Complementation of adenovirus E4 mutants by transient expression of E4 cDNA and deletion plasmids", Nucleic Acids Research 17:3037-3048, 1989.
Le Gal La Salle, G., J.J. Robert, S. Berrard, V. Ridoux, L.D. Stratford-Perricaudet, M. Perricaudet, and J. Mallet. An adenovirus vector for gene transfer into neurons and glia in the brain. *Science* 259:988-990, 1993.
Majors, J.E. Retrovirol vector-strategies and applicaitons. *Semin. Virol.* 3:285-295, 1992.
McGrory, W.J., D. S. Bautista, and F.L. Graham. A simple technique for the rescue of early region 1 mutations into infectious human adenovirus type 5. *Virology* 163:614-617, 1988.
Miller, A.D. Human gene therapy comes of age. *Nature* 357:455-460, 1992.
Morgan, R.A., L. Couture, O. Elroy-Stein, J. Ragheb, B. Moss, and W.F. Anderson. Retroviral vectors containing putative internal ribosome entry sites: development of a polycistronic gene transfer system and applications to human gene therapy. *Nucleic Acids Res.* 20:1293-1299, 1992.
Mulligan, R.C. The basic science of gene therapy. *Science* 260:9260-932, 1993.
Prevec et al., "Use of Human Adenovirus-based Vectors for Antigen Expression in Animals", *J. gen. Virol.*, 70:429-434, 1989.

(Continued)

*Primary Examiner*—Deborah Crouch
(74) *Attorney, Agent, or Firm*—Fulbright & Jaworski, LLP

(57) ABSTRACT

An adenoviral supervector system is disclosed that is capable of expressing more than 7.5 kilobases of heterologous DNA in a replication defective adenoviral vector. The supervector system comprises an adenoviral vector construct and a helper cell. The vector construct is capable of being replicated and packaged into a virion particle in the helper cell. In particular, the helper cell expresses DNA from the E2 region of the adenovirus 5 genome and complements deletions in that region in the vector construct.

In certain embodiments, the disclosed invention comprises tissue specific expression of up to 30 kb of heterologous DNA directed by an adenoviral vector. Also disclosed are methods of transferring heterologous DNA into mammalian cells.

22 Claims, 11 Drawing Sheets

OTHER PUBLICATIONS

Ragot, T., N. Vincent, P. Chafey, E. Vigne, H. Gilgenkrantz, D. Couton, J. Cartaud, P. Briand, J.-C. Kaplan, M. Perricaudet, and A. Kahn. Efficient adenovirus-mediated transfer of a human minidystrophin gene to skeletal muscle of mdx mice. *Nature* 361:647-650, 1993.

Renan, M.J. Cancer genes: current status, future prospects, and applicants in radiotherapy/oncology. *Radiother. Oncol.* 19:197-218, 1990.

Rich, D.P., L.A. Couture, L.M. Cardoza, V.M. Guiggio, D. Armentano, P.C. Espino, K.Hehir, M.J. Welsh, A.E. Smith, and R.J. Gregory. Development and analysis of recombinant adenoviruses for gene therapy of cystic fibrosis. *Hum. Gene Ther.* 4:461-476, 1993.

Rosenfeld, M.A., K. Yoshimura, B.C. Trapnell, K. Yoneyama, E.R. Rosenthal, W. Dalemans, M. Fukayama, J. Bargon, L.E. Stier, L. Stratford-Perricaudet, M. Perricaudet, W. B. Guggino, A. Pavirani, J.-P. Lecocq, and R.G. Crystal. In vivo transfer of the human cystic fibrosis transmembrane conductance regulator gene to the airway epithelium. *Cell* 68:143-155, 1992.

Rosenfeld, M.A., W. Siegfried, K. Yoshimura, K. Yoneyama, M. Fukayama, L.E. Stier, P.K. Paakko, P. Gilardi, L. Stratford-Perricaudet, M. Perricaudet, S. Jallat, A. Pavirani, J.-P. Lecocq, and R.G. Crystal. Adenovirus-mediated transfer of a recombinant α1-antitrypsin gene to the lung epithelium in vivo. *Science* 252:431-434, 1991.

Stratford-Pericaudet et al., "Feasibility of adenovirus-mediated gene transfer in vivo", *Bone Marrow Transplantation*, 9 (Suppl. 1) :151-152, 1992.

Stratford-Perricaudet et al., "Widespread Long-term Gene Transfer to Mouse Skeletal Muscles and Heart", *J. Clin. Invest.*, 90:626-630, 1992.

Stratford-Perricaudet, L.D, M. Perricaudet, and P. Briand. Evaluation of the transfer and expression in mice of an enzyme-encoding gene using a human adenovirus vector. *Hum. Gene Ther.* 1:241-256, 1990.

Su, W., T. Middleton, B. Sugden, and H. Echols. DNA looping between the origin of replication of Epstein-Barr virus and its enhancer site: stabilization of an origin complex with Epstein-Barr nuclear antigen I. *Proc. Natl. Acad. Sci. USA* 88:10870-10874, 1991.

Zhang, W.-W., X. Fang, C.D. Branch, W. Mazur, B.A. French, and J.A. Roth. Generation and identification of recombinant adenovirus by liposome-mediated transfection and PCR analysis. *BioTechiques* 15:868-872, 1993.

Casey et al., "Growth Suppression of Human Breast Cancer Cells by the Introduction of a Wild-Type p53 Gene," *Oncogene*, 6:1791-1797, 1991.

Wills and Menzel, "Adenovirus Vectors for Gene Therapy of Cancer," *Journal of Cellular Biochemistry*, p. 204, Abstract # S216, Mar.-Apr. 1993.

Carter et al., "Adenovirus Containing a Deletion of the Early Region 2A Gene Allows Growth of Adeno-Associated Virus with Decreased Efficiency," *Virology*, 191:473-476, 1992.

Bacchetti, et al, "Inhibition of Cell Proliferation by and Adenovirus Vector Expressing the Human Wild Type p53 Protein," *International Journal of Oncology*, 3:781-788, 1993.

Bowtell et al., "Comparison of Expression in Hemopoietic Cells by Retroviral Vectors Carrying Two Genes," *Journal of Virology*, 62(7):2464-2473, 1988.

Cai et al., "Stable expression of the wild-type p53 gene in human lung cancer cells after retrovirus-mediated gene transfer," *Hum. Gene Ther.*, 4:617-24, 1993.

Chiao et al., "The current state of oncogenes and cancer: experimental approaches for analyzing oncogenetic events in human cancer," *Cancer and Metastasis Review*, 9:63-80, 1990.

Colicos et al., Construction of a recombinant adenovirus containing the denV gene from bacteriophase T4 which can partially restore the DNA repair deficiency in xeroderma pigmentosum fibroblasts, *Carcinogenesis*, 12(2):249-255, 1991.

Culver, et al, "In Vivo Gene Transfer with Retroviral Vector-Producer Cells for Treatment of Experimental Brain Tumors," *Science*, 256:1550-1552, 1992.

Curiel et al., "High-efficiency gene transfer mediated by adenovirus coupled to DNA-polylysine complexes," *Human Gene Therapy*, 3:147-154, 1992.

Davidson et al., "A model system for in vivo gene transfer into the central nervous system using adenoviral vector," *Nature Genetics*, 3:219-223, 1993.

Friedmann, "Progress toward human gene therapy," *Science*, 244:1275-1281, 1989.

Fritsche et al., "Induction of nuclear accumulation of the tumor-suppressor protein p53 by DNA-damaging agents," *Oncogene*, 8:307-318, 1993. Published erratum, Oncogene, 8(9):2605, 1993.

Fujiwara et al., "Induction of chemosensitivity in human lung cancer cells in vivo by adenovirus-mediated transfer of the wild-type p53 gene," *Cancer Res.*, 54:2287-2291, 1994.

Fujiwara et al., "Induction of chemosensitivity in human lung cancer cells in vivo by adenovirus-mediated transfer of the wild-type p53 gene," *Surgical Forum*, 45:524-526, 1994.

Fujiwara et al., "A retroviral wild-type *p53* expression vector penetrates human lung cancer spheroids and inhibits growth by inducing apoptosis," *Cancer Res.*, 53:4129-4133, 1993.

Fujiwara et al., "Therapeutic effect of retroviral wild-type *p53* expression vector in an orthotopic lung cancer model," *J. Natl. Cancer Inst.*, 86(19):1458-1462, 1994.

Graham and Prevec, "Manipulation of Adenovirus Vectors," In: *Methods in Molecular Biology: Gene Transfer and Expression Protocols*, E.J. Murray (ed.), The Humana Press, Inc., vol. 7, Chapter 11, pp. 109-128, 1991.

Huber et al., "Retroviral-Mediated Gene Therapy for the Treatment of Hepatocellular Carcinoma: An Innovative Approach for Cancer Therapy," *Proc. Natl. Acad. Sci. USA*, 88:8039-8043 (1991).

Jolly, "Viral vector systems for gene therapy," *Cancer Gene Therapy*, 1(1):51-64, 1994.

Levine, "Tumor suppressor genes," *BioEssays*, 12(2):60-66, 1990.

Lotze et al., "New biologic agents come to bat for cancer therapy," *Current Opinion in Oncology*, 4:1116-1123, 1992.

Miller and Rosman, "Improved retroviral vectors for gene transfer and expression," *BioTechniques*, 7:980-990, 1989, ABSTRACT provided.

Muzyczka, "Use of adeno-associated virus as a general transduction vector for mammalian cells," *Curr. Top. Microbiol. Immunol.*, 158:98-129, 1992.

Neve, "Adenovirus Vectors Enter the Brain," *Trends Neuroscience*, 16(7):251-253, 1993.

Pardoll, "Immunotherapy with cytokine gene-transduced tumor cells: the next wave in gene therapy for cancer," *Current Opinion in Oncology*, 4:1124-1129, 1992.

Stratford-Perricaudet, "Gene Transfer into Animals: the Promise of Adenovirus," *Human Gene Transfer*, 219:51-61, 1991.

Wagner et al., "Coupling of adenovirus to transferrin-polylysine/ DNA complexes greatly enhances receptor-mediated gene delivery and expression of transfected genes," *Proc. Natl. Acad. Sci. USA*, 89:6099-6103, 1992.

Weinberg, "Tumor suppressor genes," *Science*, 254:1138-1146, 1991.

Wilkinson et al., "Constitutive and enhanced expression from the CMV major IE promoter in a defective adenovirus vector," *Nucleic Acids Research*, 20(9):2233-2239, 1992.

Wills, et al, "Tumor Supressor Gene Therapy of Cancer: Adenoviral Mediated Gene Transfer of p53 and Retinoblastoma cDNA into Human Tumor Cell Lines," J. Cell. Biochem. Supp. 18c, p. 204, 1994.

Zhang and Roth, "Propagation of Recombinant p53 Adenovirus and Evaluation of its Effect on Human Lung Cancer Cell Lines," *The Fourth Meeting of the Molecular Basis of Cancer*, Jun. 1993.

\* cited by examiner

FIGURE 11A
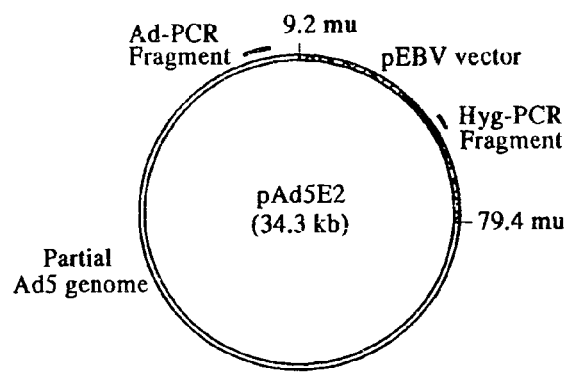
FIGURE 11B
1. Hyg-PCR primers define a 0.55-kb fragment in hygromycin B gene:
   5'-GTGTACGCCCGACAGTCCCG-3'
   5'-CCGATCTTAGCCAGACGAGC-3'
2. Ad-PCR primers define a 0.86-kb fragment in Ad5 genome at 10.98-13.38 mu:
   5'-TCGTTTCTCAGCAGCTGTTG-3'
   5'-CATCTGAACTCAAAGCGTGG-3'
FIGURE 11C
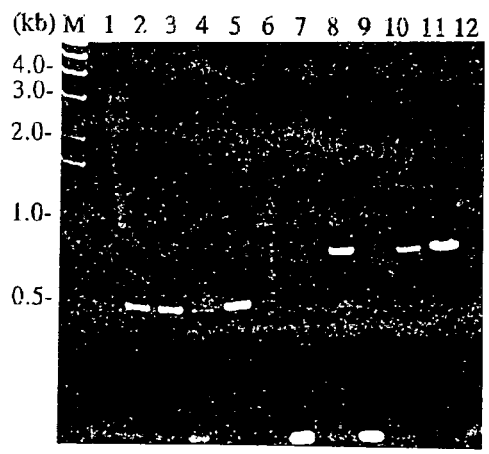
FIGURE 11D
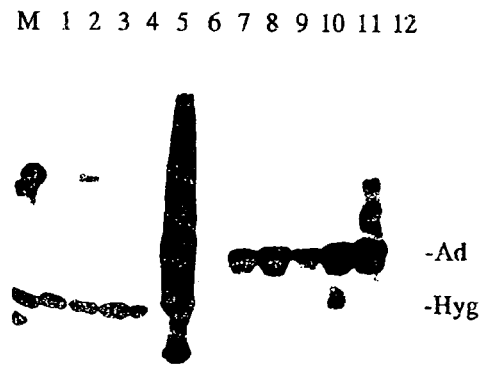

ADENOVIRUS SUPERVECTOR SYSTEM

BACKGROUND OF THE INVENTION

1. Field of the Invention

The present invention relates generally to the field of viral vectors and the use of such vectors to express foreign DNA in mammalian cells. The invention also relates to the field of gene therapy and particularly gene therapy involving viral vectors to direct genetic material to be expressed in particular tissues. More particularly, it concerns adenovirus and the ability to displace a large amount of the adenoviral genome with heterologous DNA and to replicate the viral construct in a helper cell line and express the foreign DNA in a host cell.

2. Description of the Related Art

Gene therapy is an area that offers an attractive alternative for the treatment of many diseases and disorders. In particular, the ability of viruses to enter a cell and express its genetic material in the host cell raises the possibility of replacing lost or defective gene function in vivo. However, for gene therapy to succeed, there is a need for new vectors with the properties of high therapeutic index, large capacity, targeted gene delivery, and tissue-specific gene expression. High therapeutic index indicates high therapeutic effect with low adverse effect, or in other words, a high rate of cure or improvement of the disorder with low or no side effects. This is a pharmacological concept that applies to all therapeutic agents, including gene therapy vectors. However, currently available gene transfer vectors are not able to meet the requirement of high therapeutic index (Mulligan, 1993), because of the vector-borne cycto- or geno-toxicities that are associated with many of the current gene transfer vectors.

Multiple and targeted gene transfer is particularly relevant to gene therapy for cancer (Friedmann, 1992). Throughout the last decade, studies of oncogenes and tumor suppressor genes have revealed more and more evidence that cancer is a disease developed through a process of multiple cytogenetic disorders (Chiao et al., 1990; Levine, 1990; Weinberg, 1991; Sugimura et al., 1992). Based on this concept of carcinogenesis, new strategies have developed rapidly as alternatives to conventional cancer therapy (Renan, 1990; Lotze et al., 1992; Pardoll, 1992). One of these is gene therapy (Friedmann, 1989), in which tumor suppressor genes, antisense oncogenes, and other related genes are used as therapeutic genes. Some strategies contemplated for gene therapy of cancer are the restoration of tumor-suppressor gene function, the blocking of oncogene expression and the correction of other gene-related disorders in cancer cells. It is believed that to achieve a maximal therapeutic effect, targeted delivery of a combination of these therapeutic genes by a single higher-capacity vector into cancer cells will be essential. Unfortunately, no such vector is currently available.

Another example of a disease for which a large capacity vector might be effective is Duchenne muscular dystrophy (DMD), a lethal, X-linked degenerative disorder of muscle, which affects about 1 in 35,000 newborn males. DMD is caused by a deficiency of dystrophin (Zubrzycka-Gaarn et al., 1988), a 427 kD protein encoded by a 14-kb transcript (Koenig et al., 1987). A possible therapy for this disease would be the restoration of dystrophin function by insertion and expression of the dystrophin gene in the patient's muscles (Blau, 1993; Cox et al., 1993). This therapy would require a vector that could efficiently deliver the 14 kb cDNA into muscle cells and specifically express the DMD protein in the muscle cells. Unfortunately, at the time of this disclosure, there is no vector system available which is capable of delivering more than 7.5 kb of DNA to be expressed in a specific tissue.

Retroviruses were the earliest gene transfer vectors. They were first used to insert gene markers and for transducing the cDNA of adenosine deaminase (ADA) into human lymphocytes (Miller, 1992). Unfortunately, retroviruses have several drawbacks as gene therapy agents, including genotoxicity caused by integration into the host genome, instability, dependence on target cell receptors for infection and proliferation only in actively dividing cells (Miller and Rosman, 1989; Major, 1992). In addition, the maximum gene-carrying capacity of retroviral vectors is under 10 kb (Morgenstern and Land, 1991).

Adeno-associated virus (AAV) has recently been developed as a gene transfer system. Wild-type AAV has high infectivity and specificity in integrating into the host cell genome (Hermonat and Muzyczka, 1984; Lebkowski et al., 1988). However, experimental data has shown that recombinant AAV tend to have low titers and lose their specificity of integration (Samulski et al., 1989). Also, the maximum gene-carrying capacity for AAV is under 5 kb (Walsh et al., 1992).

Herpes simplex virus type-1 (HSV-1) is attractive as a vector for applications directed to the nervous system because of its neurotropic property (Geller and Federoff, 1991; Geller, 1993). The HSV-1 genome has over 70 genes located along a 150-kb DNA molecule (Roizman and Sears, 1990), but the largest foreign DNA insertion in the virus has been 7 kb (Knipe et al., 1978). For example, a helper cell line (E5 cells) available for the propagation of replication-defective HSV-1 has complemented the 5 kb ICP4 gene (Deluca et al., 1985). However, because of its very complex genome, a much greater understanding of the interaction of HSV with host cells is required before a suitable HSV vector system can be engineered. In particular, an appropriate vector backbone has not been developed and issues related to gene expression during latency have not been resolved (Glorioso et al., 1992).

Vaccinia virus, from the poxvirus family, has also been developed as an expression vector (Moss, 1991; Moss, 1992). The vaccinia genome is among the most complex of all animal viruses, comprising approximately 200 discrete protein-coding regions along a nearly 200-kb DNA molecule (Goebel, et al., 1990). It has been shown that approximately 25 kb of foreign DNA could be inserted into the viral genome and packaged into the virion (Smith and Boss, 1983). However, the extreme cytotoxicity of vaccinia virus presents a limitation to its use in gene therapy applications. Until this is overcome, vaccinia virus will not be suitable for in vivo gene therapy. Other potential viral vectors exist (Mulligan, 1993; Kriegler, 1990), but they either are not well characterized or do not have the necessary characteristics for a supervector system.

Adenoviruses have been widely studied and well-characterized as a model system for eukaryotic gene expression. Ad are easy to grow and manipulate, and they exhibit broad host range in vitro and in vivo. This group of viruses can be obtained in high titers, e.g., $10^9$-$10^{11}$ plaque-forming unit (PFU)/ml, and they are highly infective. The life cycle of Ad does not require integration into the host cell genome. The foreign genes delivered by Ad vectors are expressed episomally, and therefore, have low genotoxicity to host cells. Ad appear to be linked only to relatively mild diseases, since there is no known association of human malignancies with Ad infection. Moreover, no side effects have been reported in studies of vaccination with wild-type Ad (Couch et al., 1963; Top et al., 1971), demonstrating their safety and therapeutic potential as in vivo gene transfer vectors.

Ad vectors have been successfully used in eukaryotic gene expression (Levrero et al., 1991; Gomez-Foix et al., 1992) and vaccine development (Grunhaus and Horwitz, 1992; Graham and Prevec, 1992). Recently, animal studies demonstrated that recombinant Ad could be used for gene therapy (Stratford-Perricaudet and Perricaudet, 1991; Stratford-Perricaudet et al., 1990; Rich et al., 1993). Successful experiments in administering recombinant Ad to different tissues include trachea instillation (Rosenfeld et al., 1991; Rosenfeld et al., 1992), muscle injection (Ragot et al., 1993), peripheral intravenous injection (Herz and Gerard, 1993), and stereotactic inoculation into the brain (Le Gal La Salle et al., 1993).

Generation and propagation of the current Ad vectors depend on a unique helper cell line, 293, which was transformed from human embryonic kidney cells by AD5 DNA fragments and constitutively expresses E1 proteins (Graham, et al., 1977). Since the E3 region is dispensable from the Ad genome (Jones and Shenk, 1978), the current Ad vectors, with the help of 293 cells, carry foreign DNA in either the E1, the E3 or both regions (Graham and Prevec, 1991). In nature, Ad can package approximately 105% of the wild-type genome (Ghosh-Choudhury, et al., 1987), providing capacity for about 2 extra kb of DNA. Combined with the approximately 5.5 kb of DNA that is replaceable in the E1 and E3 regions, the maximum capacity of the current Ad vector is under 7.5 kb, or about 15% of the total length of the vector. More than 80% of the Ad viral genome remains in the vector backbone and is the source of vector-borne cytotoxicity. Also, the replication deficiency of the E1 deleted virus is incomplete. For example, leakage of viral gene expression has been observed with the currently available Ad vectors at high multiplicities of infection (Mulligan, 1993).

Another problem with the currently available vectors is the potential for generation of wild-type virus by recombination. This may occur because the left end of the current Ad vectors has a sequence of about 1.5 kb (9.8-14 mu) overlapping with the E1 fragment in 293 cells (Graham, et al., 1977). Homologous recombinations that generate wild-type virus were detectable when E1 substitution vectors were extensively amplified in 293 cells (personal communication, Dr. Richard Gregory, CANJI, Inc., San Diego, Calif.).

Finally, Ad mutants with deletions at different regions of the viral genome have been rescued by helper viruses that provide the deleted gene products in trans. In cell line W162 (Weinberg and Ketner, 1983), which was stably transfected with the E4 region DNA, the constantly expressed E4 proteins supported propagation of E4 deletion (92-99 mu) mutants (Bridge et al., 1993). However, it has not been believed possible to delete the large E2 region which would provide for the insertion of up to 35 kb of foreign DNA into the adenoviral vector.

Therefore, there still exists an immediate need for an adenoviral supervector system which will have a high therapeutic index, a large carrying capacity of heterologous DNA and the capacity for targeted gene delivery and tissue specific expression. Such a vector system will have utility in a wide variety of in vivo and in vitro applications such a gene therapy protocols, the production of useful protein products in mammalian cell culture, as gene transfer markers or for the diagnosis of genetic deficiencies in particular cell lines.

SUMMARY OF THE INVENTION

The present invention seeks to overcome these and other drawbacks inherent in the prior art by providing an adenoviral "supervector" system wherein the E2 and, optionally, other Ad "early" gene regions have been removed. These "supervectors" have an extremely large capacity for carrying recombinant genetic material, due to the removal from them of all or part of the E2 region, which is approximately 16 kb in size, or optionally, the further removal of other early gene regions. A key aspect of the invention is the disclosure of technology for the development of helper cell lines in which these additional regions of the Ad genome are stably introduced into 293 cells or other recipient cells to establish new Ad helper cell lines. By supporting displacement of more than 80% of the remaining viral genome, cell lines such as these make possible an E2 supervector. The improvements of the E2 supervector over current Ad vector systems include the incorporation of up to 80% of the viral genome into the helper cell, a gene-delivery capacity of 30 kb, little possibility of wild type recombination and minimized vector-borne cytotoxicity.

The surprising discovery made by the present inventors that the adenoviral E2 regions could be expressed in a helper cell and would be able to complement adenoviral vectors with the corresponding regions deleted led to this invention. Before the present invention, complementation of the E2 regions of the adenoviral genome was not thought to be possible because of their size and complexity. For example, the E2A region which comprises about 6 kb, also comprises the L4 region in the reverse orientation. The E2B region, which is the largest of the early gene regions comprising about 10 kb, also comprises the major late promoter/tripartite leader region as well as the L1 gene in the reverse orientation. The tripartite leader region is a complex region of untranslated DNA that directs the cutting and splicing of the viral mRNA to direct the entire late life cycle of the virus. It is this complexity in a region that overlaps the E2B region that led to the acceptance in the art that E2B could not be deleted from adenoviral vectors. In contrast, the E1, E3 and E4 regions do not overlap any other structural regions of the genome. It is the ability to delete all these regions, E1, E3, E4 and E2 and the ability of the adenovirus to package 2 kb of extra DNA, that is made possible by the present invention and that allows the production of adenoviral "supervectors" with the capacity of carrying up to 30 kb of heterologous DNA.

An important embodiment of the present invention is a recombinant cell which expresses all or part of the E2 region of the adenoviral genome and is capable of supporting replication of an adenovirus vector construct having a corresponding E2 deletion. The recombinant cell is also referred to as the helper cell, because the expression of recombinant DNA in the cell supports replication of the viral vector. The helper cell of the present invention supports replication of the adenoviral vector by providing in trans the elements of the adenovirus genome which are necessary for the life cycle of the virus, but which have been deleted from the adenovirus vector. By in trans is meant that the adenoviral proteins are encoded on a segment of DNA that is separate from the adenovirus vector and still are available to direct the complete viral life cycle of the vector.

The helper cell of the invention is derived from a mammalian cell and preferably from a human embryonic kidney cell. Preferably, the helper cell may be derived from 293 cells and the most preferred helper cell is the Ad5E2 cell.

Although the present specification illustrates a particularly preferred helper cell, it is understood that an equivalent helper cell could be produced by one of skill in the art in light of the present invention. Any such helper cell which expresses the adenoviral genes necessary to complement in trans, deletions in the E2 region of the adenoviral genome, or which supports replication of an adenoviral vector comprising more than about 7.5 kb of heterologous DNA would also fall within the spirit and scope of the present claimed invention. For example, although primate cells are preferred and human or even human embryonic kidney cells are most preferred, any type of cell that is capable of supporting replication of the virus would be acceptable in the practice of the invention. Other cell types might include, but are not limited to Vero cells, CHO cells or any eukaryotic cells for which tissue culture techniques are established as long as the cells are adenovirus permissive. By adenovirus permissive is meant that the adenovirus is able to use the cellular environment to complete the entire intracellular virus life cycle.

As used herein, the term "recombinant" cell is intended to refer to a cell into which a recombinant gene, such as a gene from the adenoviral genome has been introduced. Therefore, recombinant cells are distinguishable from naturally occurring cells which do not contain a recombinantly introduced gene. Recombinant cells are thus cells having a gene or genes introduced through the hand of man. Within the present disclosure, the recombinantly introduced genes are from the E2 region of the adenovirus genome and are contained in a vector such as an Epstein-Barr virus-based vector, for example.

Another embodiment of the present invention is an adenovirus vector construct comprising more than 7.5 kb of heterologous DNA and wherein all or part of the E2 regions have been deleted and heterologous DNA inserted in their place, and wherein the vector construct replicates in a helper cell. The examples of preferred embodiments provided herein make use of the adenovirus 5 serotype genome, however it is understood that other serotypes such as the adenovirus type 2 genome for example, or other serotypes would also function in the practice of the invention. Prior to the present invention, the largest insert that could be contained in the vector was 5.5 kb, inserted in place of the E1 and E3 regions and including the additional 2 kb that the virus can package. Because of the present invention, up to 30 kb of heterologous DNA can be contained in the vector. The present invention makes possible for example, deletion of the E1, E2, E3 and E4 regions or any combination of these and replacement of the deleted regions with heterologous DNA.

It is understood that the adenovirus vector construct may therefore, comprise at least 10 kb or at least 20 kb or even about 30 kb of heterologous DNA and still replicate in a helper cell. By replicate in a helper cell, is meant that the vector encodes all the necessary cis elements for replication of the vector DNA, expression of the viral coat structural proteins, packaging of the replicated DNA into the viral capsid and cell lysis, and further that the trans elements are provided by the helper cell DNA. Replication is determined by contacting a layer of uninfected cells with virus particles and incubating said cells. The formation of viral plaques, or cell free areas in the cell layers is indicative of viral replication. These techniques are well known and routinely practiced in the art. It is understood that the adenoviral DNA that stably resides in the helper cell may comprise a viral vector such as an Epstein-Barr virus vector, or it may comprise a plasmid or any other form of episomal DNA that is stable, non-cytotoxic and replicates in the helper cell.

The adenovirus vector construct of the present invention will have a deletion of the adenoviral genome which is replaced with heterologous DNA. For example, the adenovirus vector construct of the present invention will have all or part of the E2 region deleted, or even deletions of the E1, E2, E3 and E4 regions of the genome or any combination of these and heterologous DNA will be inserted into the regions of the deletions. Any adenovirus vector of the present invention may also comprise 2 kb of additional DNA which is packageable in the virion capsid. Therefore, the virus vector will comprise no more than about 36 kb in order to be packaged in the virion, but the vector may comprise less than 36 kb or even less than 35 kb. In fact, no lower limit on the size of the vector has been established, except that it will contain all the cis acting elements necessary for replication.

By heterologous DNA is meant DNA derived from a source other than the adenovirus genome which provides the backbone for the vector. This heterologous DNA may be derived from a prokaryotic or a eukaryotic source such as a bacterium, a virus, a yeast, a plant or even an animal. The heterologous DNA may also be derived from more than one source. For instance, a promoter may be derived from a virus and may control the expression of a structural gene from a different source such as a mammal. Preferred promoters include viral promoters such as the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements.

The promoters and enhancers that comprise the heterologous DNA will be those that control the transcription of protein encoding genes in mammalian cells may be composed of multiple genetic elements. The term promoter, as used herein refers to a group of transcriptional control modules that are clustered around the initiation site for RNA polymerase II. Promoters are believed to be composed of discrete functional modules, each comprising approximately 7-20 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between elements is flexible, so that promoter function is preserved when elements are inverted or moved relative to one another. Depending on the promoter, it appears that individual elements can function either cooperatively or independently to activate transcription.

The heterologous DNA of the present invention may also comprise an enhancer. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities. They have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way. It is understood that any such promoter or promoter/enhancer combination may be included in the heterologous DNA of the adenoviral vector to control expression of the heterologous gene regions.

The heterologous DNA may include more than one structural gene under the control of the same or different promoters. The heterologous DNA may also include ribosome binding sites and polyadenylation sites or any necessary elements for the expression of the DNA in a eukaryotic or a mammalian cell. These vector constructs are created by methods well known and routinely practiced in the art such as restriction enzyme digestion followed by DNA ligase directed splicing of the various genetic elements. The heterologous DNA may further comprise an inducible promoter. An inducible promoter is a promoter which is inactive or exhibits low activity except in the presence of an inducer substance. Some examples of inducible promoters that may possibly be included as a part of the present invention include, but are not limited to, MT II, MMTV (mouse mammary tumor virus), Collagenase, Stromelysin, SV40, Murine MX Gene, α-2-Macroglobulin, MHC Class I Gene H-2 kb, HSP70, Proliferin, Tumor Necrosis Factor or Thyroid Stimulating Hormone a Gene. However, it is understood that any inducible promoter may be used in the practice of the invention and all such promoters/enhancers would fall within the spirit and scope of the claimed invention.

Another type of promoter that may comprise a portion of the heterologous DNA is a tissue specific promoter. A tissue specific promoter is a promoter that is active preferentially in a cell of a particular tissue type, such as in the liver, the muscle, endothelia and the like. Some examples of tissue specific promoters that may be used in the practice of the invention include the BSA promoter to be expressed in the liver or the surfactin promoter to be expressed in the lung, with the muscle creatine kinase enhancer combined with the human cytomegalovirus immediate early promoter being the most preferred for expression in muscle tissue, for example.

Another embodiment of the invention is a virion particle containing the packaged adenovirus vector construct. The virion particle is capable of and may be employed to infect cells as a means of introducing the vector DNA into cells wherein the heterologous DNA is expressed. The virion capsid may be identical in structure to the "wild type" adenovirus 5 capsid or it may be altered. Such alterations may include the incorporation of cell targeting agents such as antibodies or cell receptor recognition peptides to target the virions to particular cells.

The targeting mechanism may include the insertion in the viral capsid proteins in either the Ad helper cell or in the vector that express, e.g. a binding site peptide sequence or a ligand peptide that would serve to target the virion to a particular type of cell, or only to cells expressing certain surface proteins. One particularly useful example would be the expression of the Fc binding region from protein A on the surface of the viral capsid. These altered viruses could then be treated with an antibody specific for a certain cell or tissue type. The virus capsid would bind to the antibodies and would then be directed to the cell recognized by the antibodies. Another example is the expression of a ligand binding site on the surface of the virus. In this example, the virus would bind to the ligand on the targeted cell or tissue surface. Another example of targeting would be the expression of an epitope on the virus capsid. In this technique, the virus particles would be treated with monoclonal antibodies to the epitope conjugated with a cell or tissue targeting ligand to direct the virus to the target cell or tissue. It is also understood that the virus may be directly applied to a target area. A preparation containing the virus particles could be injected into a local area, such as an organ or into a tumor.

The invention may also be described as an adenovirus vector construct comprising at least about 200 base pairs of the left ITR region of the adenovirus genome, more than 7.5 kilobases or about 10 kilobases or about 20 kilobases or even about 30 kilobases of heterologous DNA and at least about 200 base pairs of the right ITR region of the adenovirus genome. As used herein, the adenovirus genome is the adenovirus type 5 genome as described in FIG. 1, or even the adenovirus type 2 genome. In a particular embodiment, the vector will consist essentially of map units 0-1.25 of the adenovirus 5 genome, at least 7.5 kb of heterologous DNA and map units 84.5-100 of the adenovirus 5 genome. In its most preferred embodiment, the left and right ITR regions will flank the heterologous DNA and contain said heterologous DNA between them. However, any arrangement of the viral and heterologous DNA that is able to replicate in the helper is acceptable and is included as part of the present invention.

In certain embodiments, the present invention is a method of expressing a foreign gene in a mammalian cell. This method would comprise the steps of obtaining an adenoviral vector construct comprising more than 7.5 kb of heterologous DNA, replicating the adenoviral vector construct in a helper cell, obtaining virion particles produced by the helper cells and infecting mammalian cells with the virion particles.

The foreign gene to be expressed as described in the preceding paragraph may of any origin, for example, a bacterium, a yeast, a plant, an animal or even a human gene. Preferably the adenovirus vector construct contains a deletion in the E2 region of the genome and the foreign gene is inserted in its place. In the preferred method, the helper cell would express the adenovirus E2 region DNA, thereby supporting replication of the vector. In the most preferred embodiment the helper cell is an Ad5E2 cell.

The virion plaques that would be produced by the replicating viral vector and would thus lyse the host cell can be obtained by any acceptable means. Such means would include filtration, centrifugation or preferably physical touching of viral plaques. All such methods of obtaining virion particles and infecting mammalian cells with the particles are well known to those of skill in the art.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 4A and 4B show the electrophoretic analysis of H5dl1011 DNA replication and capsid protein accumulation in pAdh clones. This figure is an autoradiogram of agarose gel electrophoresis of the low molecular weight DNA isolated from the Vc, V1.1 and V1.2 cells that were infected with H5dl1011 at 5 PFU/cell for 24 hours and then radiolabeled with $^{32}P$ for 24 hours. DNA sources and treatments are indicated at the top of each lane.

FIG. 4B. This figure is an SDS-PAGE analysis of the protein samples of cells that were infected with H5dl1011 at 5 PFU/cell for 36 hours and then radiolabeled with [$^{35}S$]-Methionine for 24 hours. Protein sources are indicated at the top of each lane. Roman numerals indicate the viral capsid proteins accumulated in the V1.1 cells.

FIG. 11A. This figure is a drawing of the pAd5E2 vector showing the location of the PCR priming sites used in characterizing the vector and cell lines.

FIG. 11B. This figure defines the PCR primers used in characterizing the vector and cell lines. The sequences in this figure are designated in order from top to bottom as SEQ ID NOS:1-4.

FIG. 11C. This figure is an agarose gel showing the results of the PCR amplification of the Ad5E2 cells and vectors.

FIG. 11D. This figure is a Southern blot analysis of the agarose gel from FIG. 11C with the $^{32}P$ labeled pAd5E2 probe.

DETAILED DESCRIPTION OF THE PREFERRED EMBODIMENTS

The design and development of the Ad supervector system is an unexpected breakthrough in the development of vectors for gene transfer. The new system will not only substantially increase the gene-delivery capacity of Ad vectors, but will also greatly improve their therapeutic potential, since the replacement of most of the viral genome eliminates the vector-borne cytotoxicity and the possibility of wild-type recombination that are associated with the current Ad vector systems. Because the design of the helper cell line and supervector is focused on meeting the current and future demands for gene delivery, the system will have a wide range of applications in the fields of gene therapy and gene transfer.

Gene therapy generally involves three principal elements: therapeutic genes, delivery systems, and target cells. One of the urgent technical challenges in gene therapy technology is how to specifically deliver and controllably express the therapeutic genes in target cells in vivo. Since no currently available delivery system can accomplish this (Mulligan, 1993), there is a great demand for a new system with this capacity.

Figure 1:
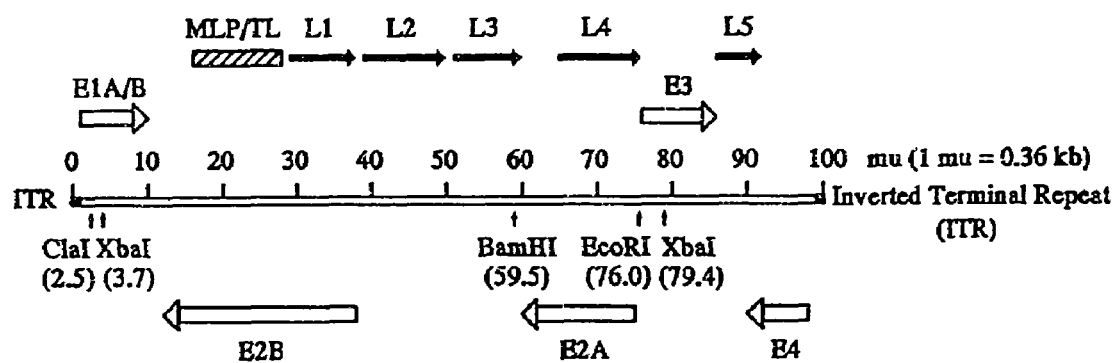
FIG. 1. This figure depicts the structure of the Ad5 genome. The genome is divided into 100 map units (mu). The open arrows represent early (E) transcription and the solid arrows represent late (L) transcription. The direction of transcription is indicated by arrows. Gaps in arrows indicate intervening sequences. The hatched box represents location of major late promoter and tripartite leader sequences (MLP/TL). The numbers in parenthesis indicate the map units.

Adenovirus (Ad), is particularly suitable for use as a gene transfer vector because of its mid-sized genome, ease of manipulation, high titer, wide target-cell range, and high infectivity. Adenoviruses are double-stranded DNA viruses with a linear genome of approximately 36 kb. A simplified map of the adenovirus type 5 (Ad5) genome with a few key landmarks is diagrammed in FIG. 1. Both ends of the viral genome contain 100-200 base pair (bp) inverted terminal repeats (ITR), which are cis elements necessary for viral DNA replication and packaging. The early (E) and late (L) regions of the genome that contain different transcription units are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNAs issued from this promoter possess a 5' tripartite leader (TL) sequence which makes them preferred mRNAs for translation.

It is known that a part of the adenoviral genome can be replaced by foreign DNA and the virus can still replicate in helper cells that supply the proteins encoded by the displaced viral genome in trans. The currently available Ad vectors carry foreign DNA in either early region 1 (E1) or 3 (E3) or both, and are replicated primarily in the 293 cell line, a transformed human embryonic kidney cell line that constitutively expresses E1 proteins (Graham et al., 1977; Graham and Prevec, 1991). However, the recombinant DNA capacities of the vectors generated in this system are limited to 7.5 kb. In addition, a helper cell line designated as W162 (derived from Vero cells), carries an intact adenovirus E4 region and is able to support the replication of adenovirus with deletions in the E4 region. However, the W162 cell line will support deletions of only on the order of 1-3 kb. Moreover, both these systems are subject to vector-borne cytotoxicity and the possibility of wild-type recombination, since most (more than 80%) of the wild-type viral genome remains in the vectors.

In order to improve the current Ad vector systems, an Ad supervector system was designed. This system comprises novel Ad vectors and their helper cell lines that can generate greatly improved recombinant viruses with properties such as greater gene-delivery capacity, higher therapeutic potential, targeted gene delivery, and when appropriately modified, tissue-specific gene expression. The Ad supervector system is designed so that up to 35 kb of the Ad viral genome between the inverted terminal repeats (ITR) can be replaced by foreign DNA. Removing large segments of the viral genome affords the added advantage of greatly improving the therapeutic potential of the current Ad vector systems, since the lack of viral DNA in the vector eliminates the vector-borne cytotoxicity and the possibility of wild-type recombination that are associated with the current Ad vector systems.

This large displacement of DNA is possible because the cis elements required for viral DNA replication and packaging are all found by the inventors to be localized in the inverted terminal repeats (100-200 bp) at either end of the linear viral genome. For example, the origins of replication for Ad DNA are localized in the ITR of the viral genome, and replication is uniquely primed by the covalently bound terminal protein at each 5' end. This suggests asymmetric replication of a unit-length linear molecule and that linear unit-length molecules are the likely substrate for viral packaging. In addition, the packaging signal for viral encapsidation is localized between 194-385 bp (0.5-1.1 m.u.) at the left end of the viral genome (Hearing et al., 1987). This signal mimics the protein recognition site in bacteriophage λ DNA where a specific sequence close to the left end but outside the cohesive end sequence mediates the binding to proteins that are required for insertion of the DNA into the head structure. E1 substitution vectors of Ad have demonstrated that a 450 bp (0-1.25 u) fragment at the left end of the viral genome was enough to direct packaging in 293 cells (Levrero et al., 1991).

The first step in the generation of the supervector system is the production of new Ad helper cell lines. The Ad helper cell line is the stably transfected or transformed cell line that carries episomally maintained genomic fragments of Ad. These cell lines can express different sets of Ad proteins and can be used to generate and propagate different recombinant Ad vectors. Prior to the present invention, such helper cells were able to support viral vectors containing deletions in the E1, E3 or E4 regions. However, owing to the genetic complexity and sheer size of the E2 region, it was believed that E2 region functions could not be successfully complemented by a helper cell host producer of those functions. The production of the helper cells of the present invention, e.g. Ad5E2, has now made it possible to support adenoviral vectors with up to 30 kb of genomic DNA deletions.

Preferred helper cell lines are derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include e.g. Vero cells or other monkey embryonic mesenchymal or epithelial cells.

The second step in the supervector system is the construction of adenoviral "supervectors." The vectors are generated by displacing the DNA which is expressed in the helper cells with foreign DNA. Prior to the present invention, the largest possible displacement was approximately 7 kb, but the supervector system allows the displacement of up to 35 kb of DNA from the adenoviral genome.

The Ad supervectors are circular or linear DNA molecules that comprise essential cis elements for Ad DNA replication and packaging (such as ITR and the packaging signal) and heterologous DNA. The heterologous DNA may be, but is not limited to polypeptide encoding regions and their control elements for expression and regulation in mammalian cells, which may include, but are not limited to various promoters/enhancers, including tissue-specific promoters or enhancers, polyadenylation signals, splicing signals, 5' or 3' translational regulatory elements, elements for stable transfection and selection, and the like. The heterologous DNA fragments may be from different sources, in different lengths, and arranged in different combinations depending on the application. The supervectors also comprise the necessary genetic elements to direct their packaging into recombinant Ad viruses after transfection into the Ad helper cells.

The third step in the generation of the supervector system is the production of recombinant Ad viruses (superviruses). The superviruses can be generated by transfection of the supervector into the helper cell line and propagation of the virus. These viruses are genetically and structurally engineered viruses that carry heterologous genes and regulatory elements. They may have modified surface structures that allow them to escape from host immune response and to be targeted to certain cells, for example. These viruses are replication-defective and helper-virus-dependent. The viruses produced from this system are contemplated to have little cytotoxicity and no possibility of wild-type recombination. This system will have a wide range of applications including targeted gene-delivery of the Ad vector, tissue-specific expression of the genes expressed from the Ad vector and inducible or stable expression of Ad vector genes. The advantages of this supervirus system are tabulated in Table 1.

TABLE 1

Comparison of currently available vectors and the super Ad vector system.

| Ad vector system | Helper cell line | Viral genome helper | Viral genome vector | Gene-delivery capacity | Wild-type recombination | Vector-borne cytotoxicity |
|---|---|---|---|---|---|---|
| Current | 293 | 11% | 84% | 7.5 kb | possible | present |
| Super | Ad5E2 | 80% | 17% | 30 kb | no | minimized |

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Plasmid pCEP4 Vector Transfected Cells

The vector to be used for the stable expression of the partial Ad genome must meet certain technical requirements such as high genetic carrying capacity, high copy number, and long term expression. One such vector is an Epstein-Barr virus-based eukaryotic expression vector, pCEP4 (Invitrogen Corp., San Diego, Calif.). This vector has the Epstein-Barr viral nuclear antigen (EBNA-1) and origin of replication (oriP) and exhibits high-copy episomal replication and produces high levels of recombinant proteins in a wide range of mammalian cells (Yates, et al., 1985; Su, et al., 1991). This vector also comprises the hygromycin resistance gene for clonal selection and stable maintenance of the vector in cells.

Figure 2:
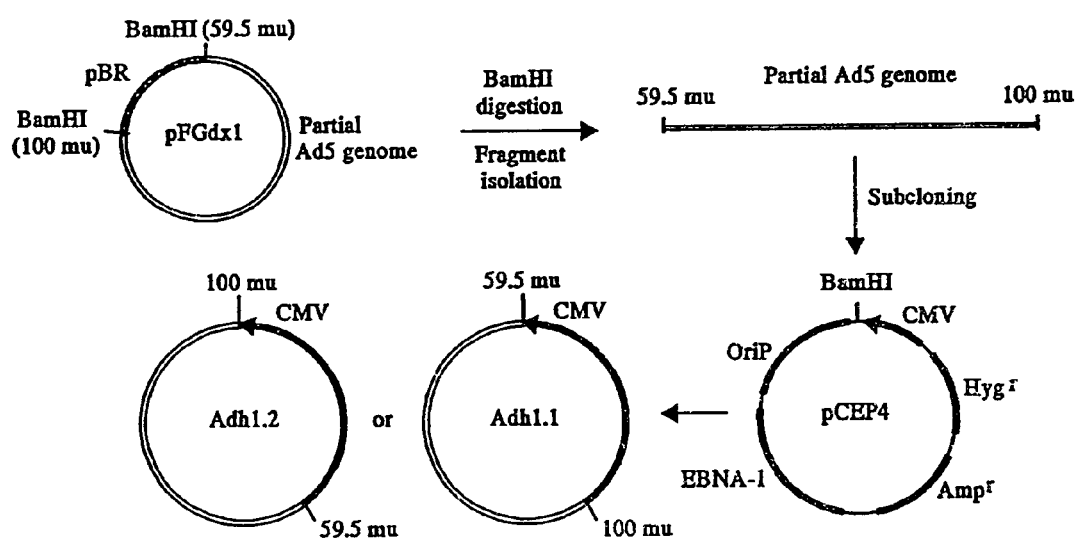
FIG. 2. This figure is a flow diagram of the generation of the Adh1 vectors. The 59.5-100 mu fragment was isolated from the plasmid pFGdx1 (Haj-Ahmad and Graham, 1986) and inserted into pCEP4 vector, resulting in Adh1.1 or Adh1.2.

A 14.6-kb DNA fragment (59.5-100 mu with E3 deleted) that covers the intact E4 and L5 regions of the Ad5 genome was isolated from the plasmid pFGdx1 (Haj-Ahmad and Graham, 1986), which was kindly provided by Dr. Frank L. Graham at McMaster University, Hamilton, Ontario, Canada. This fragment was inserted at the BamHI cloning site of pCEP4, producing the pAdh1.1 and pAdh1.2 vectors which differ by opposite orientations of the respective fragments to the CMV promoter in pCEP4 (FIG. 2). The expression vectors were transfected into Vero cells by liposome-mediated transfection with DOTAP (Boehringer-Mannheim Corp., Indianapolis, Ind.) (Zhang, et al., 1993). Vero is an African green monkey kidney cell line. Vero cells were the preferred cell line for the expression of the pAdh vectors because this cell line was previously used to create the Ad E4 complementing cell line (W162) by stable transfection with the Ad5 84-100 mu fragment (Weinberg and Ketner, 1983). Transfection of the cells with the original pCEP4 vector was used as a control. After transfection and growth in the presence of hygromycin B, the antibiotic-resistant clones were selected.

EXAMPLE 2

Complementation of the E4 Gene

Figure 3:
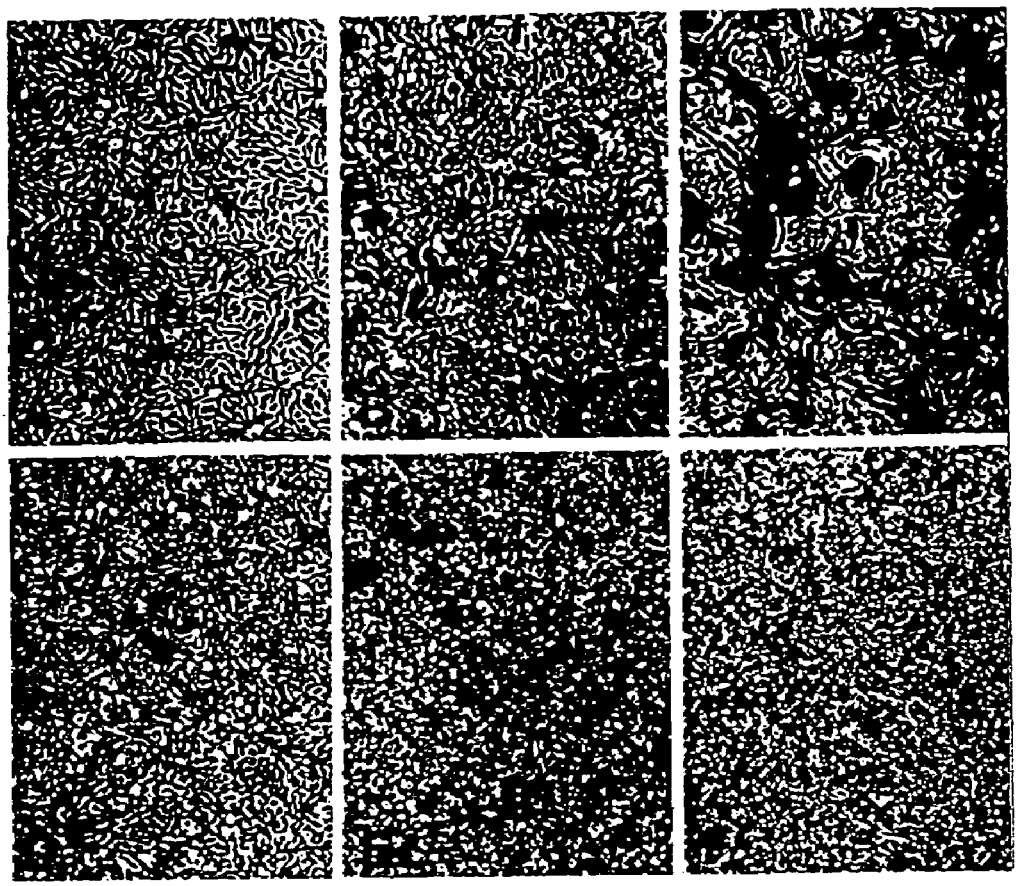
FIG. 3. This figure shows the morphology of pAdh-transfected Vero cells and the result of H5dl1011 infection. These are phase-contrast images of the Vero transfectants (100×). Top row, left to right are vector transfected Vero cells (Vc); pAdh1.2 transfected Vero cells (V1.2); and pAdh1.1 transfected Vero cells (V1.1). Bottom row left to right are Vc cells infected with H5dl1011; V1.2 cells infected with H5dl1011; and V1.1 cells infected with H5dl1011. The H5dl1011 viruses were used at 5 PFU/cell. Cytopathic effect of Ad is obvious in H5dl1011 infected V1.1 cells at 48 hours after infection.
Figure 4A:
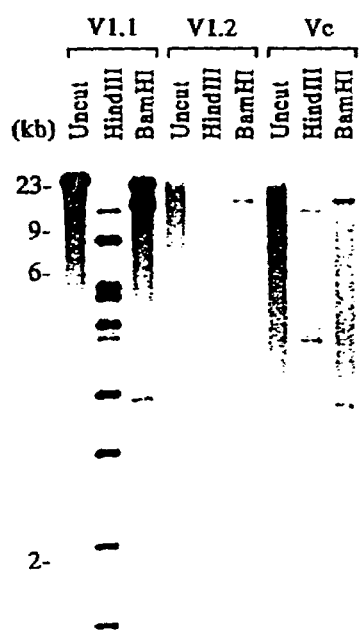
FIG. 4A.
Figure 4B:

The pAdh1 vectors described in Example I contain the entire E4 and L5 regions from an Ad5 genomic fragment and are expected to complement Ad mutants with deletions or mutations in those regions of the genome. Functional assays were designed to examine whether the cells could support the propagation of the Ad5 E4 deletion mutant, H5dl1011 (Bridge, et al., 1993), kindly provided by Dr. Gary Ketner at Johns Hopkins University, Baltimore, Md. The selected clones were treated with the H5dl1011 virus at a multiplicity of infection (moi) of 5. The cytopathic effect of Ad was used as an indicator for the propagation of the virus in the clones. It was shown that the clones of the Vero cells that contained the pAdh1.1 vector (referred to as V1.1 cells) were capable of supporting the propagation of H5dl1011. The clones of the Vero cells that contained the pAdh1.2 vector (referred to as V1.2 cells) could not support the propagation of H5dl1011, nor could the Vero cells that contained pCEP4 vector alone (referred to as Vc cells). FIG. 3 shows the morphology of the pAdh-clones of the Vero cells and that of the cells infected with H5dl1011. FIG. 4 demonstrates the detection of the viral DNA replication and viral capsid protein accumulation in V1.1 cells after infection with the H5dl1011 virus.

The lack of complementation of H5dl1011 by the pAdh1.2 vector is contemplated to be due to the location of the CMV promoter upstream of the E4 promoter. The lack of complementation may be caused by promoter interference between the CMV and the E4 promoters, or by an inactivation of the E4 promoter through some inhibition of the CMV promoter. The pAdh1.1 vector, with no additional promoter inserted upstream of the E4 promoter, complemented H5dl1011 much like the E4 complementing cell line W162 (Weinberg and Ketner, 1983), which also does not have a promoter upstream of the E4 promoter. Even though heterologous promoters are indicated in certain embodiments, such as when the Ad promoters are not strong enough to maintain a high-level expression of the Ad genes or when inducible expression of the genes are required, these results suggest that the interaction of the two promoters must be considered.

EXAMPLE 3

Construction of the Ad5E2 Expression Vector

The Ad5E2 expression vector was designed so that the E2 promoter activation would be dependent on the E1 proteins provided by the host cells and the E4 proteins encoded by the supervector. Therefore, the vector contains no additional promoter for the E2 fragment.

Figure 5:
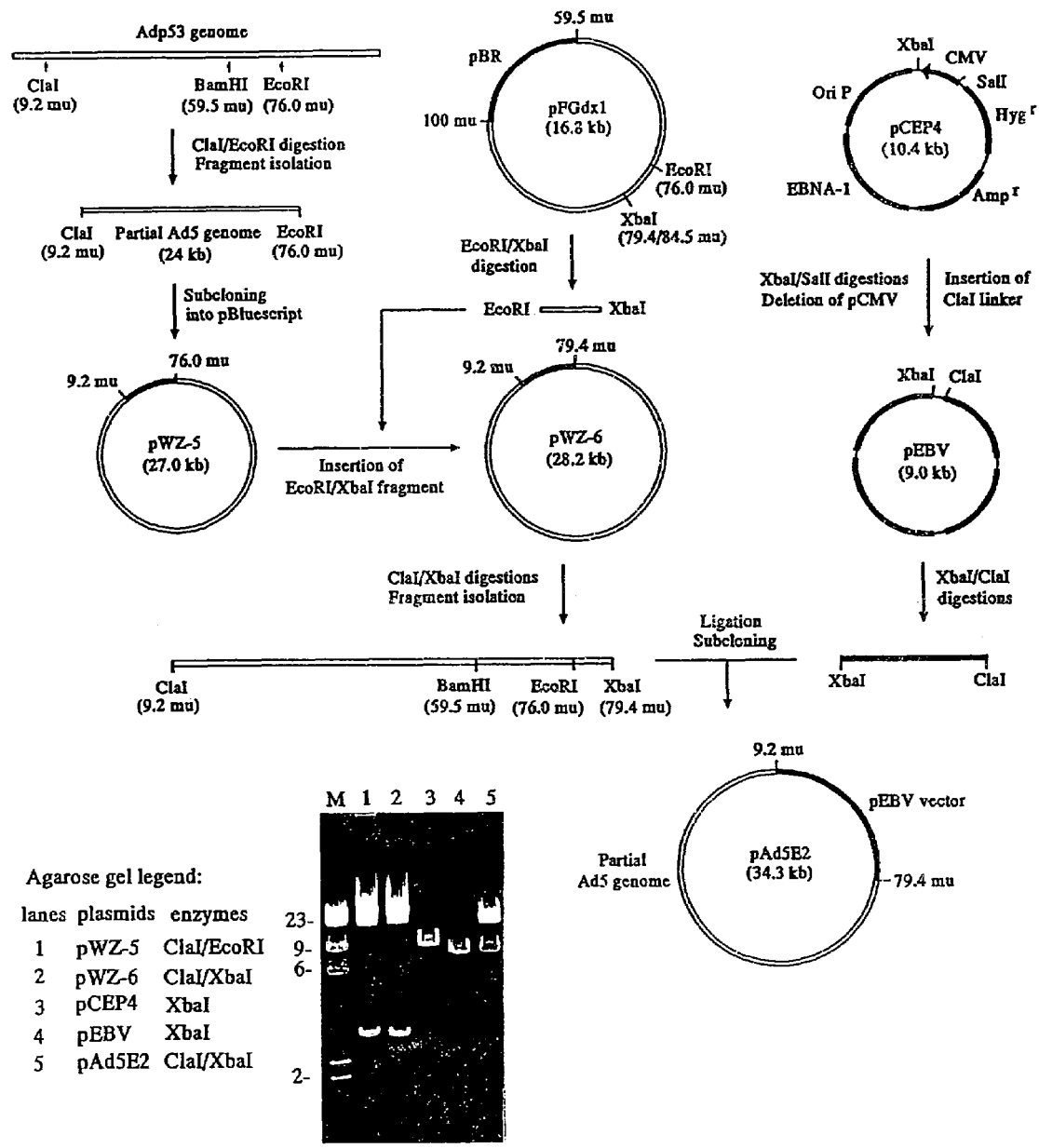
FIG. 5. This figure is a flow chart for the generation of plasmid pAd5E2 and shows the restriction analysis of the indicated plasmids.

The first step in the construction of the Ad5E2 vector was the preparation of the Ad5 E2 fragment (9.2-79.4 mu). The 9.2-76.0 mu fragment isolated from Ad5CMV-p53 DNA was first subcloned into the pBluescript (Stratagene Corp., San Diego, Calif.) derived plasmid designated pWZ-5 (FIG. 5). The 76.0-79.4 mu fragment was isolated from the plasmid pFGdx1 (Haj-Ahmad and Graham, 1986) and inserted into the pWZ-5 plasmid that already contained the 9.2-76.0 mu fragment. The resulting construction was designated pWZ-6 by the inventors and comprised the 9.2-79.4 mu E2 fragment in a pBluescript backbone (FIG. 5).

The second step was the preparation of the modified pCEP4 vector, pEBV. The pCEP4 vector (Invitrogen Corp.), contains the genetic "cassette" which has the CMV promoter sequence and the SV40 polyadenylation signal in a form convenient for the expression of inserted genes. For the construction of the Ad5E2 expression vector, the CMV promoter and the SV40 polyadenylation signal were deleted from pCEP4, resulting in the vector designated pEBV (FIG. 5). The pEBV vector retained the hygromycin-resistant gene for clonal selection and the Epstein-Barr viral origin of replication (OriP) and nuclear antigen (EBNA-1) for high-copy episomal replication.

The final step in the construction of the Ad5E2 expression vector was the isolation of the E2 fragment from pWZ-6 and insertion of that fragment into the pEBV vector (FIG. 5). The resultant vector, pAd5E2, contains intact transcriptional units for the E2A, E2B, and L1-L4 regions of the Ad5 genome. The length of the E2 fragment is defined by the map units 9.2 and 79.4, which are the break points for foreign DNA insertions into the currently used E1 or E3 substitution Ad vectors (Graham and Prevec, 1992). This indicates that the E2 fragment between these two points may be a partial Ad genome and may function as an independent genomic unit.

The agarose gel in FIG. 5 shows the results of the digestion of the various plasmids with the indicated restriction enzymes. The pAd5E2 expression vector DNA was prepared in a large scale culture and purified by CsCl-gradient, and was used for transfection in the production of the Ad helper cell line.

EXAMPLE 4

Production of the Ad5E2 Cell Line

The pAd5E2 expression vector was transfected into 293 cells by liposome (DOTAP)-mediated transfection according to the manufacturer's protocol (Boehringer Mannheim, Indianapolis, Ind.) and as described previously (Zhang, et al., 1993). To improve the transfection efficiency, 293 cells were cultured to the exponential growth phase. The cells were harvested and inoculated into multiple 24-well plates with $10^5$ cells/well which gave about 80' confluency the next day. Transfection mixtures were prepared in the ratio of 15 µg of pAd5E2 DNA or 5 µg of pEBV DNA (control) to 30 µl of DOTAP per 6 ml Eagle's MEM supplemented with 10% horse serum. Each plate required 24 ml of the mixture (1 ml/well). 293 cells treated with DOTAP with no vectors were used as a control for hygromycin B selection.

Figure 6:
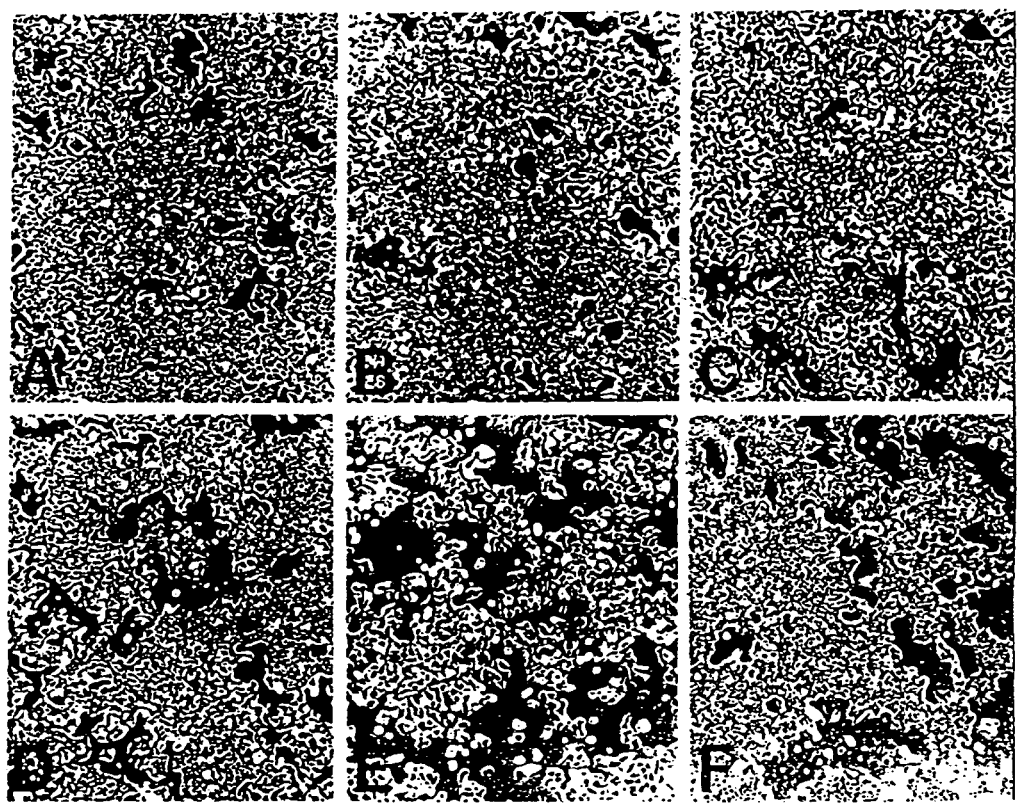
FIG. 6. This figure is phase contrast images showing the morphology differences among the parental and transfected cells. The top left panel is 293 parental cells. The top center panel is pEBV transfected cells. The following panels are individual clones of the pAd5E2 vector transfected cells.

Twenty-four hours after transfection, the cells were selected with 100 µg/ml of hygromycin B in Eagle's MEM supplemented with 10% horse serum. The concentration of hygromycin B was gradually increased to 200 µg/ml over 2 weeks. The antibiotic-resistant cell clones were transferred to 60-mm, followed by 100-mm culture dishes. After this amplification, aliquots of the cells from each clone were frozen in 90% horse serum with 10% DMSO and stored in liquid nitrogen. The rest of the cells were maintained in the medium with 200 µg/ml hygromycin B for further study. FIG. 6 is magnified images of the Ad5E2 cell clones, the parental 293 cells and "vector only" control cells.

EXAMPLE 5

Functional Analysis of Ad5E2 Cells

Figure 7:
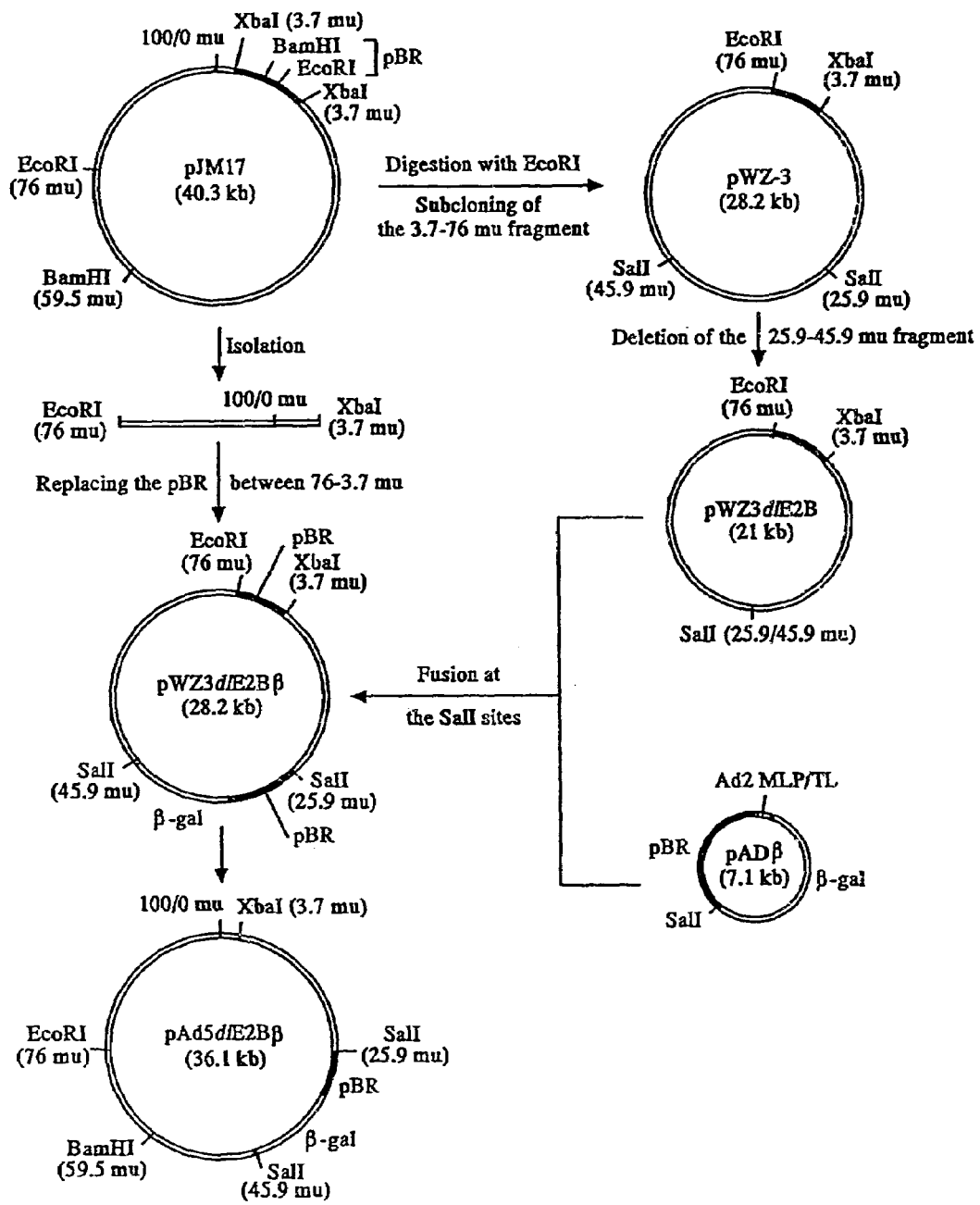
FIG. 7. This figure is a flow diagram of the generation of the Ad5E2B vector.

This example describes studies that demonstrate the efficiency of the Ad5E2 cells in complementing E2 deletions or substitutions. For the purposes of the studies, an E2B substitution mutant was constructed and designated Ad5 E2B. This E2 mutant was derived from the pJM17 plasmid (McGrory, et al., 1988), a circularized form of the Ad5 genome with an insertion of the pBR322 plasmid at 3.7 mu. This circularized Ad genome was created by the connection of its ITR regions (0/100 mu fusion) and has been demonstrated to be functional (Graham, 1984). A 7-kb Ad5 genomic fragment between the SalI sites at 25.9 and 45.9 mu was deleted from pJM17 by digestion with SalI, ligation of the isolated large fragment, and subcloning (FIG. 7). This deletion included the E2B, L1, and L2 genes from the Ad5 genomic sequence. A 7.1-kb plasmid, pAdβ (CLONTECH), which contains the *E. coli* β-galactosidase gene under the control of the Ad2 major late promoter (MLP) was added into the deletion site. The β-galactosidase gene was then used as a reporter gene to monitor the transfection efficiency of the Ad5 E2B substitution vector into Ad5E2 cells.

The plasmid pWZ-3 was previously constructed by digesting pJM17 with EcoRI, isolating the larger fragment, and inserting the 3.7-76 mu fragment of the Ad5 genome (FIG. 7). The plasmid pWZ3dlE2B is then generated from pWZ-3 by deleting the fragment between the SalI sites at 25.9 and 45.9 mu. The pAdβ plasmid is then fused with pWZ3dlE2B at their respective SalI sites, which produces the 28.2 kb plasmid designated pWZ3dlE2Bβ. Finally, the ITR fusion fragment (76-100/0-3.7 mu) is isolated from pJM17 and replaces the pBR sequence from pWZ3dlE2Bβ, producing pAd5dlE2Bβ.

The pAd5dlE2Bβ vector is then transfected into Ad5E2 cells by liposome (DOTAP)—mediated transfection. The transfected cells will be maintained in the hygromycin B selection medium for observation of cytopathic effect, which is a sign of cytotoxicity typically manifested by the Ad-infected cells. The cytopathic effect manifests as a broken cell monolayer and cell clumps formed by the sick cells which are easily seen in a light microscope. The presence of the cytopathic effect in the transfected cells indicates that complementation has been achieved.

To determine whether the pAd5E2 vector is retained in the cells, low molecular weight DNA was isolated from the cells and analyzed by PCR (See FIGS. 11A-11D). The DNA samples were analyzed with two pairs of primers that are specific for the hygromycin B gene and the Ad5 genome, respectively. The gels in FIGS. 11C-D confirm the retention of the vector in the cells. Lanes 1-6 are Hyg-PCR products of Ad5E2:1-4, pAd5E2 positive control and a no DNA negative control. Lanes 7-12 are Ad-=PCR products in the same order. FIG. 11D is the southern blot of the gel using a $^{32}$P-labeled pAd5E2 probe.

EXAMPLE 6

Design of a Super Reporter Vector

The supervector design utilizes the fusion of the Ad left and right end inverted terminal repeat (ITR) regions to create a circular plasmid vector which comprises the reporter genes. Since all the E1, E2, and L1-L4 gene products are provided in trans by the Ad helper cells, the left arm of the Ad genome in the supervector will be trimmed to be as short as 450 bp (0-1.25 mu). This has been demonstrated to be sufficient as a cis element to support E1 substitution mutants (Levrero, et al., 1991). The right arm of the Ad genome in the supervector will contain the region from 84.5 mu to 100 mu. This reduction in size will delete the E3 genes, which are known to be unnecessary for replication (Jones and Shenk, 1978). This design will eliminate the possibility of wild-type recombination, since there will be no overlap between the right arm in the supervector and the E2 fragment (9.2-79.4 mu) in the Ad5E2 cells.

Figure 8:
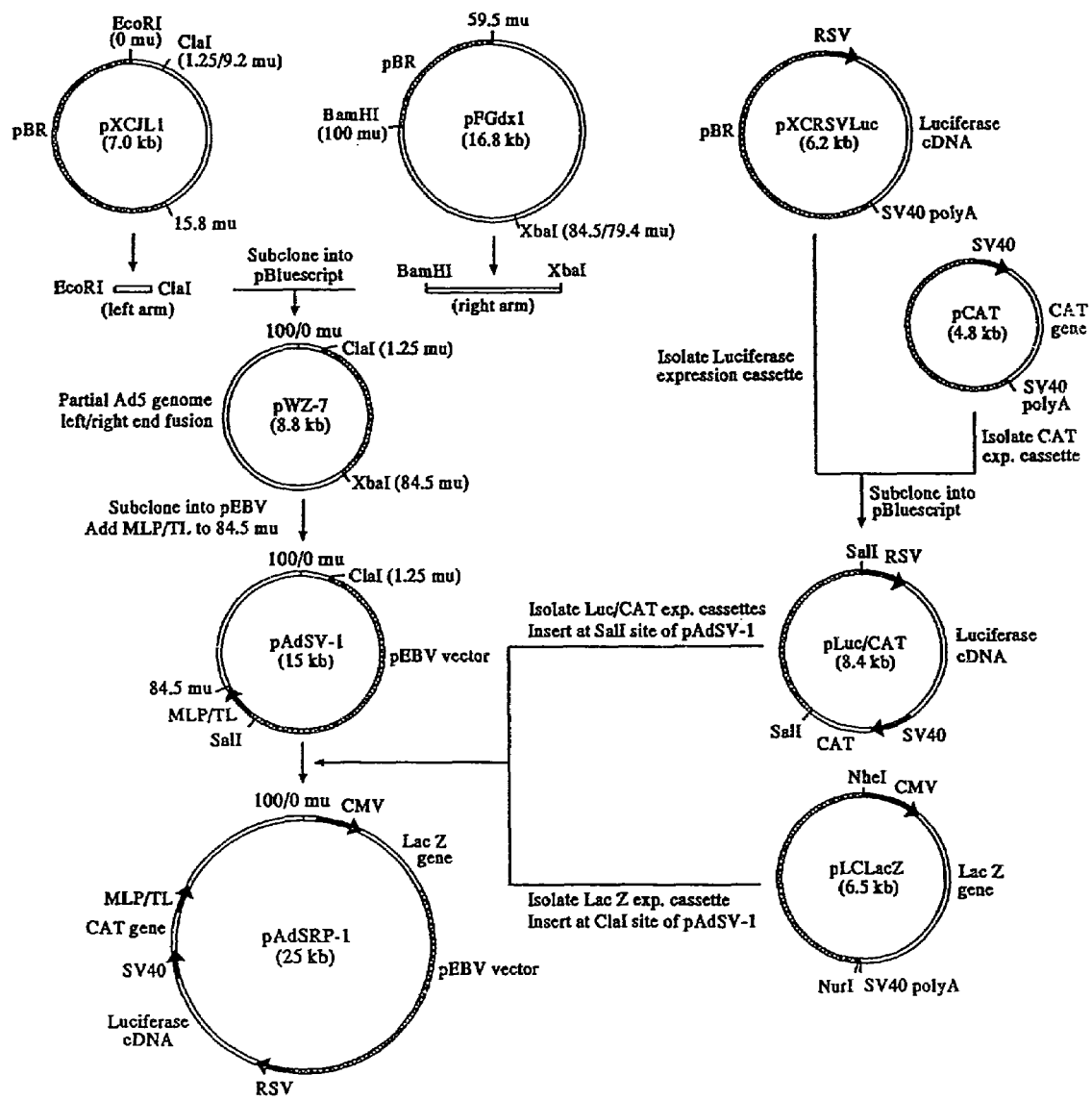
FIG. 8. This figure is a flow diagram of the generation of the Ad supervector.

The generation of the reporter supervector is diagrammed in FIG. 8. The left (0-1.25 mu) and right (84.5-100 mu) arms of the Ad5 genome will be isolated from plasmid pXCJL.1 (Frank L. Graham) and pFGdx1, respectively (FIG. 8). These two fragments will be connected through the ITR and subcloned into a pBluescript plasmid to create the plasmid designated as pWZ-7. The fused Ad arms (85.4-100/0-1.25 mu fragment) will be further subcloned into the pEBV vector. To ensure the correct expression of the L5 region that is located at 86-91.3 mu, the cassette containing the Ad2 major late promoter with the tripartite leader (MLP/TL) (Levrero, et al., 1991), kindly provided by Michel Perricaudet (Institut Gustave Roussy, Villejuif, France), will be inserted at 84.5 mu of the right arm to produce a basic supervector designated as pAdSV-1 (15 kb).

To test the capability of the supervector to carry foreign DNA, reporter genes such as LacZ, CAT, and luciferase will be inserted at the cloning sites of pAdSV-1, which will produce pAdSRP-1 (about 25 kb), a supervector that carries multiple reporter genes. The reporter supervector DNA will be prepared in large scale culture and purified by CsCl-gradient to be used for high efficiency transfection.

A potential problem in production of the supervector is the packaging of a vector of this size in helper cells. Systematic studies of packaging-size constraints have not been reported, mainly because there is no appropriate complementing cell line. However, Ad DNA from 50 to 1050% of the genome length can be stably packaged (Jones and Shenk, 1978; Larsen, 1982). In addition, defective virions are often made that have only the left end of the viral genome. These truncated viral DNA can be as short as 5% of genome length, but they appear to be able to deliver their DNA into susceptible cells (Hammarskjold, et al., 1977). Therefore, there may not be a lower limit on the size of the shortened DNA that can be successfully packaged and expressed.

The initial design for the insertion of reporter genes is to put each reporter gene in its own expression cassette. This arrangement will allow each reporter gene to be expressed independently. If the simple array of multiple gene expression cassettes does not work efficiently, an internal ribosome entry site from picornavirus (Morgan, et al., 1992) may be used to link the multiple genes. Another possible arrangement is a multiple gene array resembling the polycistron controlled by the MLP.

EXAMPLE 7

Generation of a Supervirus

Generation of the supervirus of this system depends on the efficient transfection of the Ad helper cells by the supervector DNA. Highly efficient plasmid DNA transfection into the helper cells has been achieved in the inventor's laboratory by calcium-phosphate precipitation (Dai, 1992) and liposome-mediated transfection (Zhang, et al., 1993). The following example describes a procedure for the generation and identification of a supervirus.

The Ad5E2 cells will be cultured to exponential phase and inoculated into 24-well plates at $10^5$ cell/ml, which will result in 80% confluency per well the next day. The transfection mixture is prepared in a ratio of 15 μg of the supervector (pAdSRP-1), 30 μl of DOTAP, and 6 ml of medium. This mixture will be used to transfect the Ad5E2 cells with 1 ml of transfection mixture per well for 24 hr. After transfection the cells will be maintained in Eagle's MEM supplemented with 10% horse serum. In 12-15 days after transfection, the cytopathic effect may be observed in the cell monolayers, which indicates the generation of new virus in the transfectants.

PCR analysis (U.S. Pat. No. 4,683,202, incorporated herein by reference) of DNA samples prepared from the supernatants of cell cultures with the cytopathic effect will be used to identify the newly generated Ad superviruses (Zhang, et al., 1993). The genomic structure of the superviruses will also be analyzed by PCR. The superviruses will be plaque-purified and amplified in the Ad5E2 cell line. The supervirus DNA will be obtained from the cells and purified by CsCl-gradient banding. The purified viral DNA can be analyzed by restriction mapping to confirm the viral genomic structure. The propagation of the supervirus in the Ad5E2 cells will be studied by [$^{32}$P]-labeling to detect viral DNA replication and by [$^{35}$S]-methionine incorporation to measure viral capsid protein accumulation in the cells. The efficiency of the supervirus propagation in the cells will be determined by viral titering in plaque assays.

EXAMPLE 8

Tissue-Specific Expression Ad Vector

Figure 9:
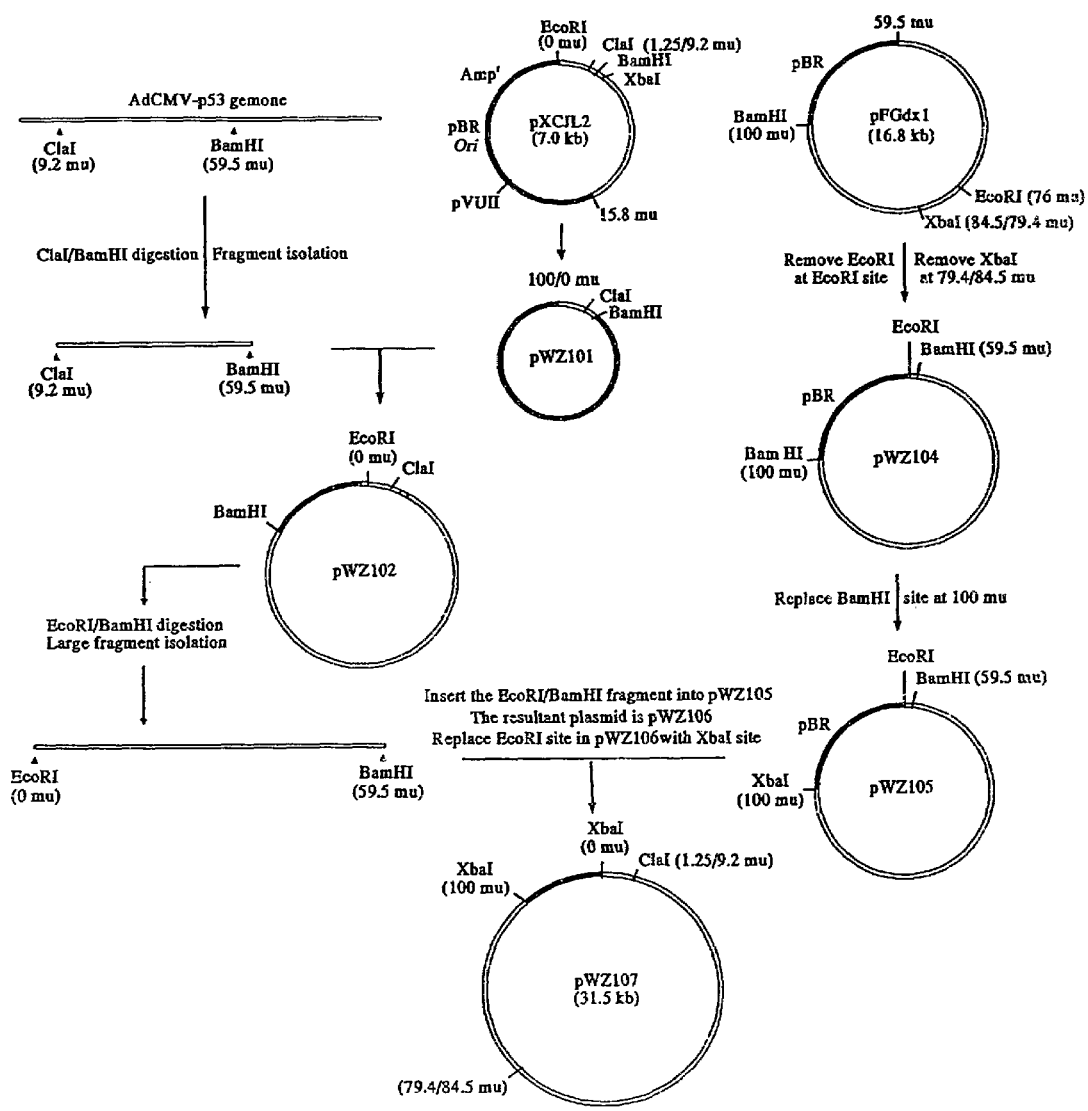
FIG. 9. This figure is a flow diagram of the generation of an E1 and E3 deletion adenoviral plasmid vector.

This example illustrates the construction of a plasmid form of the Ad5 genome containing E1 and E3 deletions. The vector is constructed from two Ad-genome-derived plasmids, pFGdx1 (Haj-Ahmad and Graham, 1986) and pXCJL2 (kindly provided by Dr. Frank L. Graham), and the recombinant p53 adenovirus (Zhang, et al., 1993). The pXCJL2 plasmid contains the 0-15.8 mu fragment of the Ad5 genome. It has a polylinker located at 1.25 mu. A large portion of this plasmid is deleted by restriction enzyme digestion of the plasmid with XbaI and PvuII followed by religation to create plasmid pWZ101 (FIG. 9). The 9.2-59.5 mu fragment of the Ad5 genome is removed from the p53 adenovirus and inserted at the ClaI and BamHI sites of the polylinker of pWZ101 to generate plasmid pWZ102.

In a second branch of this synthesis, the pFGdx1 plasmid will be modified at several restriction sites to generate plasmid pWZ105 (FIG. 9). This plasmid contains the modified 59.5-100 mu fragment of the Ad5 genome, which is flanked by the EcoRI and BamHI restriction enzyme sites. Then the EcoRI-BamHI fragments of pWZ105 and pWZ102 are removed from their respective plasmids and joined to create plasmid pWZ106. The EcoRI site in pWZ106 will be replaced by an XbaI site, resulting in the plasmid pWZ107.

This will be a basic Ad vector that can be further modified to construct a tissue-specific vector, by the insertion of tissue-specific enhancer/promoter regulatory elements at the ClaI site. The plasmid represents a great improvement over the current Ad vectors in that PWZ107 has the pBR322 origin of replication and the ampicillin resistance gene located between the 0 and 100 mu positions. This region can be easily excised by XbaI digestion before transfection of the vector into an Ad E1 helper cell such as 293.

Figure 10:
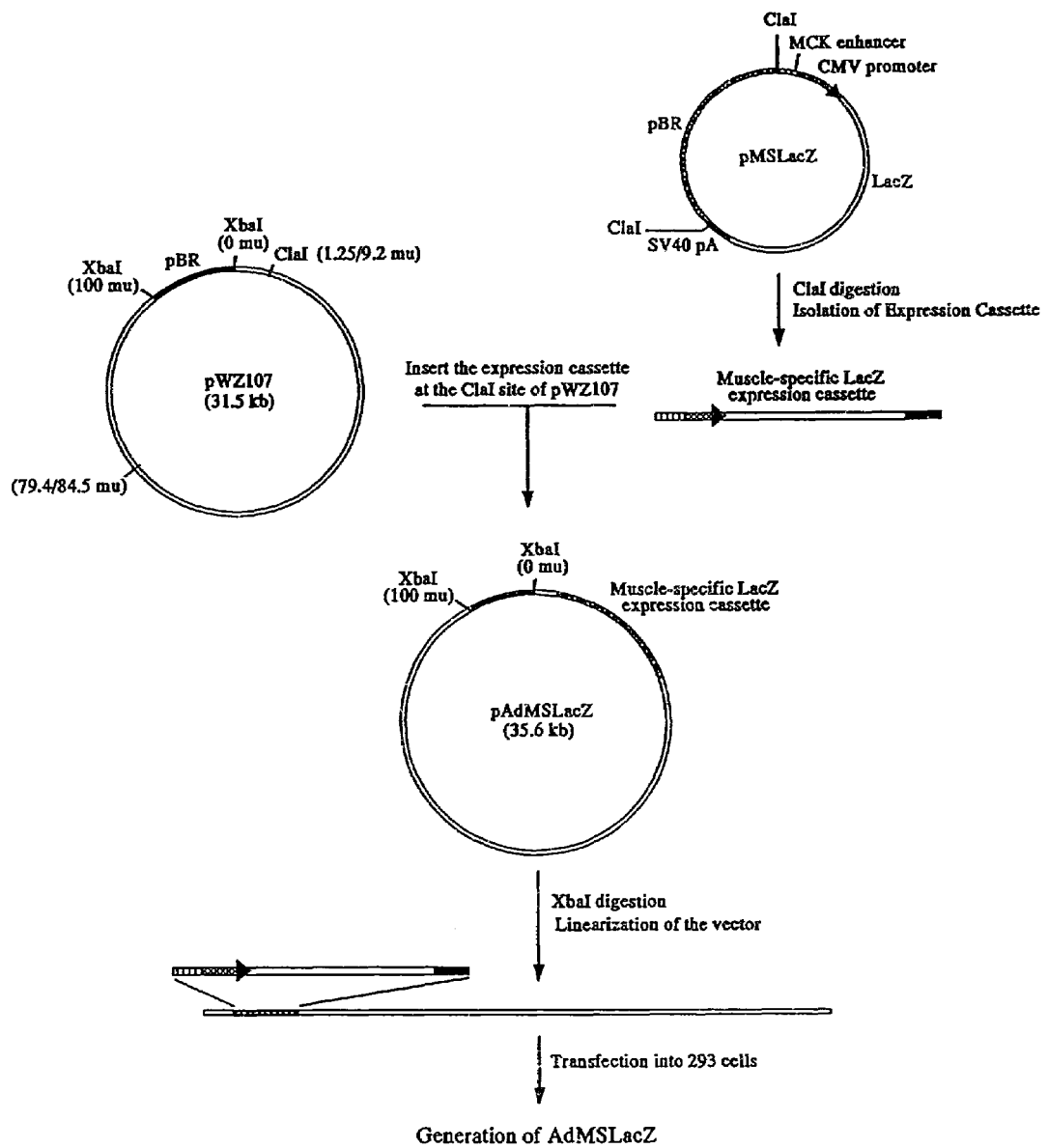
FIG. 10. This figure is a flow diagram of the generation of a muscle-specific adenoviral plasmid vector.

The tissue-specific expression of a given reporter gene is dependent upon tissue-specific regulatory elements. The plasmids created in the practice of the present invention allow one to utilize an expression cassette to express the β-gal protein in muscle cells. As shown in FIG. 10, the mouse muscle creatine kinase (MCK) enhancer (−1256 to −1050) (Dai, et al, 1992) will be connected to the human cytomegalovirus (CMV) immediate-early gene promoter (Boshart, et al, 1985) to form a chimeric regulatory element. This element will be placed upstream of the lacZ gene which is followed by an SV40 polyadenylation signal, thus forming a tissue-specific expression cassette. The cassette will be incorporated into the plasmid pAdMSLacZ by the ClaI sites at either end. The expression cassette can be readily isolated by digestion with ClaI and inserted at the ClaI site in the pWZ107 vector. This will generate the muscle specific Ad vector (pAdMSLacZ) for the muscle specific expression of the β-gal protein. The plasmid is then prepared in large scale culture and purified by CsCl-gradient for transfection.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Berkner, K. L. 1988. Development of adenovirus vectors for the expression of heterologous genes. *BioTechniques* 6: 616-629.

Blau, H. M. 1993. Muscular dystrophy: Muscling in on gene therapy. *Nature* 364: 673-675.

Boshart, J., F. Weber, G. Jahn, K. Dorsch-Hasler, B. Fleckenstein, and W. Schaffner. 1985. A very strong enhancer is located upstream of an immediate early gene of human cytomegalovirus. *Cell* 41: 521-530.

Bridge, E., S. Medghalchi, S. Ubol, M. Leesong, and G. Ketner. 1993. Adenovirus early region 4 and viral DNA synthesis. *Virology* 193: 7994-801.

Chiao, P. J., F. Z. Bischoff, L. C. Strong, and M. A. Tainsky. 1990. The current state of oncogenes and cancer: experimental approaches for analyzing oncogenetic events in human cancer. *Cancer Metastasis Rev.* 9: 63-80.

Couch, R. B., R. M. Chanock, T. R. Cate, D. J. Lang, V. Knight, and R. J. Huebner. 1963. Immunization with types 4 and 7 adenovirus by selective infection of the intestinal tract. *Am. Rev. Resp. Dis.* 88: 394-403.

Cox, G. A., N. M. Cole, K. Matsumura, S. F. Phelps, S. D. Hauschka, K. P. Campbell, J. A. Faulkner, and J. S. Chamberlain. 1993. Overexpression of dystrophin in transgenic mdx mice eliminates dystrophic symptoms without toxicity. *Nature* 364: 725-729.

Dai, Y., M. Roman, R. K. Naviaux, and I. M. Verma. 1992. Gene therapy via primary myoblasts: long-term expression of factor IX protein following transplantation in vivo. *Proc. Natl. Acad. Sci. USA* 89: 10892-10895.

Deluca, N. A., A. M. McCarthy, and P. A. Schaffer. 1985. Isolation and characterization of deletion mutants of herpes simplex virus type 1 in the gene encoding immediate-early regulatory protein ICP4. *J. Virol.* 56: 558-570.

Friedmann, T. 1989. Progress toward human gene therapy. *Science* 244: 1275-1281.

Friedmann, T. 1992. Gene therapy of cancer through restoration of tumor-suppressor functions? *CANCER* 70 (Suppl): 18101-1817.

Geller, A. I. 1993. Herpesviruses: expression of genes in postmitotic brain cells. *Curr. Opin. Genet. Devel.* 3: 81-85.

Geller, A. I., and H. J. Federoff. 1991. The use of HSV-1 vectors to introduce heterologous genes into neurons: implications for gene therapy. In: *Human Gene Transfer*, Eds, O. Cohen-Haguenauer and M. Boiron, pp. 63-73, Editions John Libbey Eurotext, France.

Ghosh-Choudhury, G., Y. Haj-Ahmad, and F. L. Graham. 1987. Protein IX, a minor component of the human adenovirus capsid, is essential for the packaging of full-length genomes. *EMBO J.* 6: 1733-1739.

Glorioso, J. G., W. F. Goins, and D. J. Fink. 1992. Herpes simplex virus-based vectors. *Semin. Virol.* 3: 265-276.

Goebel, S. J., G. P. Johnson, M. E. Perkus, S. W. Davis, J. P. Winslow, and E. Paoletti. 1990. The complete DNA sequence of vaccinia virus. *Virology* 179: 247-266.

Gomez-Foix, A. M., W. S. Coats, S. Baque, T. Alam, R. D. Gerard, and C. B. Newgard. 1992. Adenovirus-mediated transfer of the muscle glycogen phosphorylase gene into hepatocytes confers altered regulation of glycogen. *J. Biol. Chem.* 267: 25129-25134.

Graham, F. L., and L. Prevec. 1991. Manipulation of adenovirus vectors. In: Methods in Molecular Biology (Vol. 7), *Gene Transfer and Expression Protocols*, ed. E. J. Murray, The Humana Press Inc., Clifton, N.J.

Graham, F. L., J. Smiley, W. C. Russell, and R. Nairn. 1977. Characteristics of a human cell line transformed by DNA from human adenovirus type 5. *J. Gen. Virol.* 36: 59-72.

Graham, F. L. 1984. Covalently closed circles of human adenovirus DNA are infectious. *EMBO J.* 3: 3917-2922.

Graham, F. L., and L. Prevec. 1992. Adenovirus-based expression vectors and recombinant vaccines. *Biotechnology* 20: 363-390.

Grunhaus, A., and M. S. Horwitz. 1992. Adenoviruses as cloning vectors. *Semin. Virol.* 3: 237-252.

Haj-Ahmad, Y., and F. L. Graham. 1986. Development of a helper-independent human adenovirus vector and its use in the transfer of the herpes simplex virus thymidine kinase gene. *J. Viol.* 57: 2267-274.

Hammarskjold, J.-L., G. Winberg, E. Norrby, and G. Wadell. 1977. Isolation of incomplete adenovirus 16 particles containing viral and host cell DNA. *Virology* 82: 449-461.

Hearing, P., R. J. Samulsi, W. L. Wishart, and T. Shenk. 1987. Identification of a repeated sequence element required for efficient encapsidation of the adenovirus type 5 genome. *J. Virol.* 67: 2555-2558.

Hermonat, P. L., and N. Muzyczka. 1984. Use of adeno-associated virus as a mammalian DNA cloning vector: transduction of neomycin resistance into mammalian tissue culture cells. *Proc. Natl. Acad. Sci. USA* 81: 6466-6470.

Herz, J., and R. D. Gerard. 1993. Adenovirus-mediated transfer of low density lipoprotein receptor gene acutely accelerates cholesterol clearance in normal mice. *Proc. Natl. Acad. Sci. USA* 90: 2812-2816.

Horwitz, M. S. 1990. Adenoviridae and their replication. In: *Virology* (2nd Edn), eds. B. N. Field, D. M. Knipe, R. M. Chanock, J. L. Melnick, M. S. Hirsch, T. P. Monath, B. Roizman. pp. 1679-1721. Raven Press, New York.

Jones, N., and T. Shenk. 1978. Isolation of deletion and substitution mutants of adenovirus type 5. *Cell* 13: 181-188.

Knipe, D. M., W. T. Ruyechan, B. Roizman, and I. W. Halliburton. 1978. Molecular genetics of herpes simplex virus: demonstration of regions of obligatory and non-obligatory identity within diploid regions of the genome by sequence replacement and insertion. *Proc. Natl. Acad. Sci. USA* 75: 3896-3900.

Koenig, M., E. P. Hoffman, C. J. Bertelson, A. P. Monaco, C. Feener, and L. M. Kunkel. 1987. Complete cloning of the Duchenne muscular dystrophy (DMD) cDNA and preliminary genomic organization of the DMD gene in normal and affected individuals. *Cell* 50: 509-517.

Kriegler, M. P. 1990. *Gene Transfer and Expression: A Laboratory Manual*. pp. 23-61. Stockton Press, New York.

Larsen, S. H. 1982. Evolutionary variants of mouse adenovirus containing cellular DNA sequences. *Virology* 116: 573-580.

Le Gal La Salle, G., J. J. Robert, S. Berrard, V. Ridoux, L. D. Stratford-Perricaudet, M. Perricaudet, and J. Mallet. 1993. An adenovirus vector for gene transfer into neurons and glia in the brain. *Science* 259: 988-990.

Lebkowski, J. S., M. M. McNally, T. B. Okarma, and L. B. Lerch. 1988. Adeno-associated virus: a vector system for efficient introduction and integration of DNA into a variety of mammalian cell types. *Mol. Cell. Biol.* 8: 3988-3996.

Levine, A. J. 1990. Tumor suppressor genes. *BioEssays* 12: 60-66.

Levrero, M., V. Barban, S. Manteca, A. Ballay, C. Balsamo, M. L. Avantaggiati, G. Natoli, H. Skellekens, P. Tiollais, and M. Perricaudet. 1991. Defective and nondefective adenovirus vectors for expressing foreign genes in vitro and in vivo. *Gene* 101: 195-202.

Lotze, M. T., J. T. Rubin, and H. J. Zeh. 1992. New biologic agents come to bat for cancer therapy. *Curr. Opin. Oncol.* 4: 1116-1123.

Majors, J. E. 1992. Retroviral vector-strategies and applications. *Semin. Virol.* 3: 285-295.

McGrory, W. J., D. S. Bautista, and F. L. Graham. 1988. A simple technique for the rescue of early region 1 mutations into infectious human adenovirus type 5. *Virology* 163: 614-617.

Miller, A. D., and G. J. Rosman. 1989. Improved retroviral vectors for gene transfer and expression. *BioTechniques* 7: 980-990.

Miller, A. D. 1992. Human gene therapy comes of age. *Nature* 357: 455-460.

Morgan, R. A., L. Couture, O. Elroy-Stein, J. Ragheb, B. Moss, and W. F. Anderson. 1992. Retroviral vectors containing putative internal ribosome entry sites: development of a polycistronic gene transfer system and applications to human gene therapy. *Nucleic Acids Res.* 20: 1293-1299.

Morgenstern, J. P., and H. Land. 1991. Choice and manipulation of retroviral vectors. In: *Methods in Molecular Biology (Vol. 7), Gene Transfer and Expression Protocols*, ed. E. J. Murray, The Humana Press Inc., Clifton, N.J.

Moss, B. 1992. Poxviruses as eukaryotic expression vectors. *Semin. Virol.* 3: 277-283.

Moss, B. 1991. Vaccinia virus: a tool for research and vaccine development. *Science* 252: 1662-1667.

Mulligan, R. C. 1993. The basic science of gene therapy. *Science* 260: 9260-932.

Mullis, K., U.S. Pat. No. 4,683,202,

Pardoll, D. 1992. Immunotherapy with cytokine gene-transduced tumor: the next wave in gene therapy for cancer. *Curr. Opin. Oncol.* 4: 1124-1129.

Ragot, T., N. Vincent, P. Chafey, E. Vigne, H. Gilgenkrantz, D. Couton, J. Cartaud, P. Briand, J.-C. Kaplan, M. Perricaudet, and A. Kahn. 1993. Efficient adenovirus-mediated transfer of a human minidystrophin gene to skeletal muscle of mdx mice. *Nature* 361: 647-650.

Renan, M. J. 1990. Cancer genes: current status, future prospects, and applicants in radiotherapy/oncology. *Radiother. Oncol.* 19: 197-218.

Rich, D. P., L. A. Couture, L. M. Cardoza, V. M. Guiggio, D. Armentano, P. C. Espino, K. Hehir, M. J. Welsh, A. E. Smith, and R. J. Gregory. 1993. Development and analysis of recombinant adenoviruses for gene therapy of cystic fibrosis. *Hum. Gene Ther.* 4: 461-476.

Roizman, R., and A. E. Sears. 1990. Herpes simplex viruses and their replication, In: *Virology*, (2nd ed), eds. B. N. Field, D. M. Knipe, R. M. Chanock, J. L. Melnick, M. S. Hirsch, T. P. Monath, B. Roizman. pp. 1795-1841. Raven Press, New York.

Rosenfeld, M. A., K. Yoshimura, B. C. Trapnell, K. Yoneyama, E. R. Rosenthal, W. Dalemans, M. Fukayama, J. Bargon, L. E. Stier, L. Stratford-Perricaudet, M. Perricaudet, W. B. Guggino, A. Pavirani, J.-P. Lecocq, and R. G. Crystal. 1992. In vivo transfer of the human cystic fibrosis transmembrane conductance regulator gene to the airway epithelium. *Cell* 68: 143-155.

Rosenfeld, M. A., W. Siegfried, K. Yoshimura, K. Yoneyama, M. Fukayama, L. E. Stier, P. K. Paakko, P. Gilardi, L. Stratford-Perricaudet, M. Perricaudet, S. Jallat, A. Pavirani, J.-P. Lecocq, and R. G. Crystal. 1991. Adenovirus-mediated transfer of a recombinant α1-antitrypsin gene to the lung epithelium in vivo. *Science* 252: 431-434.

Sambrook et al. (1989). *Molecular cloning: A laboratory manual*. Cold Spring Harbor Laboratory. Cold Spring Harbor, N.Y.

Samulski, R. J., L.-S. Chang, and T. Shenk. 1989. Helper-free stock of recombinant adeno-associated viruses: normal integration does not require viral gene expression. *J. Virol.* 63: 3822-3828.

Smith, G. L., and B. Moss. 1983. Infectious poxvirus vectors have capacity for at least 25,000 base pairs of foreign DNA. *Gene* 25: 21-28.

Stratford-Perricaudet, L. D., M. perricaudet, and P. Briand. 1990. Evaluation of the transfer and expression in mice of an enzyme-encoding gene using a human adenovirus vector. *Hum. Gene Ther.* 1: 241-256.

Stratford-Perricaudet, L., and M. Perricaudet. 1991. Gene transfer into animals: the promise of adenovirus. p. 51-61, In: *Human Gene Transfer*, Eds, O. Cohen-Haguenauer and M. Boiron, Editions John Libbey Eurotext, France.

Su, W., T. Middleton, B. Sugden, and H. Echols. 1991. DNA looping between the origin of replication of Epstein-Barr virus and its enhancer site: stabilization of an origin complex with Epstein-Barr nuclear antigen I. *Proc. Natl. Acad. Sci. USA* 88: 10870-10874.

Sugimura, T., M. Terada, J. Yokota, S. Hirohashi, and K. Wakabayashi. 1992. Multiple genetic alterations in human carcinogenesis. *Environ. Health Perspect.* 98: 5-12.

Top, F. H., Jr., El. L. Buescher, W. H. Bancroft, and P. K. Russell. 1971. Immunization with live types 7 and 4 adenovirus vaccines. II. Antibody response and protective effect against acute respiratory disease due to adenovirus type 7. *J. Infect. Dis.* 124: 155-160.

Walsh, C. E., J. M. Liu, X. Xiao, N. S. Young, A. W. Nienhuis, and R. J. Samulski. 1992. Regulated high level expression of a human T-globin gene introduced into erythroid cells by an adeno-associated virus vector. *Proc. Natl. Acad. Sci. USA* 89: 7257-7261.

Weinberg, D. H., and G. Ketner. 1983. A cell line that supports the growth of a defective early region 4 deletion mutant of human adenovirus type 2. *Proc. Natl. Acad. Sci. USA* 80: 5838-5386.

Weinberg, R. A. 1991. Tumor suppressor genes. *Science* 254: 1138-1146.

Yates, J. L., N. Warren, and B. Sugden. 1985. Stable replication of plasmids derived from Epstein-Barr virus in various mammalian cells. *Nature* 313: 812-815.

Zhang, W.-W., X. Fang, C. D. Branch, W. Mazur, B. A. French, and J. A. Roth. 1993. Generation and identification of recombinant adenovirus by liposome-mediated transfection and PCR analysis. *BioTechniques* 15: 868-872.

Zubrzycka-Gaarn, E. E., D. E. Bulman, G. Karpati, A. H. M. Burghes, B. Belfall, H. J. Klamut, J. Talbot, R. S. Hodges, P. N. Ray, and R. G. Worton. 1988. The Duchenne muscular dystrophy gene product is localized in sarcolemma of human skeletal muscle. *Nature* 333: 466-469.

What is claimed is:

1. An adenovirus vector construct, wherein all of the E2 coding region has been deleted from the adenovirus genome and heterologous DNA is inserted in its place, but excluding an adenovirus vector from which each of the E1, E2, E3 and E4 coding regions have been deleted.

2. The adenovirus vector construct of claim 1, wherein said vector comprises more than 7.5 kb of heterologous DNA.

3. The adenovirus vector construct of claim 2, wherein said vector comprises at least 10 kb of heterologous DNA.

4. The adenovirus vector construct of claim 3, wherein said vector comprises at least 20 kb of heterologous DNA.

5. The adenovirus vector construct of claim 4, wherein said vector comprises about 30 kb of heterologous DNA.

6. The adenovirus vector construct of claim 1, wherein said heterologous DNA comprises one or more genes.

7. The adenovirus vector construct of claim 6, wherein said one or more genes are under the control of a promoter.

8. The adenovirus construct of claim 7, wherein said one or more genes are expressed in a eukaryotic cell.

9. The adenovirus vector construct of claim 7, wherein said promoter is an inducible promoter.

10. The adenovirus vector construct of claim 7, wherein said promoter is a tissue specific promoter.

11. An adenovirus vector construct consisting essentially of map units 0-1.25 of the adenovirus 5 genome, at least 7.5 kb of heterologous DNA and map units 84.5-100 of the adenovirus 5 genome.

12. A virion particle containing the packaged adenovirus vector construct of claim 1 or 11.

13. The adenovirus vector construct of claim 1, wherein only the E2 region is deleted.

14. The adenovirus vector construct of claim 1, wherein the E2 and E1 regions are deleted.

15. The adenovirus vector construct of claim 1, wherein the E2 and E3 regions are deleted.

16. The adenovirus vector construct of claim 1, wherein the E2 and E4 regions are deleted.

17. The adenovirus vector construct of claim 1, wherein the E2, E3 and E4 regions are deleted.

18. The adenovirus vector construct of claim 1, wherein the E2, E3 and E1 regions are deleted.

19. The adenovirus vector construct of claim 1, wherein the E2, E4 and E1 regions are deleted.

20. The adenovirus vector construct of claim 6, further comprising at least 10 kb of heterologous DNA.

21. The adenovirus vector construct of claim 20, further comprising at least about 20 kb of heterologous DNA.

22. The adenovirus vector construct of claim 21, further comprising about 30 kb of heterologous DNA.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:1:

GTGTACGCCC GACAGTCCCG     20

(2) INFORMATION FOR SEQ ID NO:2:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:2:

CCGATCTTAG CCAGACGAGC     20

(2) INFORMATION FOR SEQ ID NO:3:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:3:

TCGTTTCTCA GCAGCTGTTG     20

(2) INFORMATION FOR SEQ ID NO:4:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:4:

CATCTGAACT CAAAGCGTGG     20